United States Patent
Gomurashvili et al.

(10) Patent No.: US 8,445,007 B2
(45) Date of Patent: May 21, 2013

(54) BIS-(α-AMINO)-DIOL-DIESTER-CONTAINING POLY (ESTER AMIDE) AND POLY (ESTER URETHANE) COMPOSITIONS AND METHODS OF USE

(75) Inventors: Zaza D. Gomurashvili, La Jolla, CA (US); Jonathan Macferran Hughes, Carlsbad, CA (US); Jie Da, San Diego, CA (US); Huashi Zhang, San Diego, CA (US)

(73) Assignee: Medivas, LLC, San Diego, CA (US)

( * ) Notice: Subject to any disclaimer, the term of this patent is extended or adjusted under 35 U.S.C. 154(b) by 1180 days.

(21) Appl. No.: 12/066,998

(22) PCT Filed: Sep. 22, 2006

(86) PCT No.: PCT/US2006/037331
§ 371 (c)(1),
(2), (4) Date: Jul. 31, 2008

(87) PCT Pub. No.: WO2007/035938
PCT Pub. Date: Mar. 29, 2007

(65) Prior Publication Data
US 2008/0299174 A1    Dec. 4, 2008

Related U.S. Application Data

(60) Provisional application No. 60/719,950, filed on Sep. 22, 2005, provisional application No. 60/839,219, filed on Aug. 21, 2006.

(51) Int. Cl.
*A61F 2/00* (2006.01)
*A01N 25/08* (2006.01)

(52) U.S. Cl.
USPC .................................. 424/426; 424/409

(58) Field of Classification Search
USPC ........................................ 424/409, 426
See application file for complete search history.

(56) References Cited

U.S. PATENT DOCUMENTS

| | | | |
|---|---|---|---|
| 2002/0015720 A1* | 2/2002 | Katsarava et al. | 424/426 |
| 2004/0063606 A1 | 4/2004 | Chu et al. | |

FOREIGN PATENT DOCUMENTS

| | | |
|---|---|---|
| WO | WO 02/18477 A2 | 3/2002 |
| WO | WO 2005/112587 A2 | 12/2005 |
| WO | WO 2006/088647 A1 | 8/2006 |

OTHER PUBLICATIONS

Okada et al (Journal of Applied Polymer Science, vol. 62, Iss 13, 1996, pp. 2257-2265).*

* cited by examiner

*Primary Examiner* — Benjamin Packard
(74) *Attorney, Agent, or Firm* — Nixon & Vanderhye P.C.

(57) ABSTRACT

The present invention provides biodegradable, biocompatible bis-(α-amino acyl)-diol-diester-containing poly(ester amide) (PEA) and poly(ester urethane) (PEUR) co-polymer compositions with mechanical properties that can be readily tailored by selection of various combinations and proportions of the building blocks of the co-polymers. The compositions are suitable for use in production of drug-releasing biodegradable particles and implantable surgical devices, such as stents and internal fixation devices. The co-polymer compositions, particles and surgical devices biodegrade in vivo by enzymatic action to release bioactive agents in a controlled manner over time as well as biocompatible breakdown products, including one to multiple different amino acids.

24 Claims, No Drawings

BIS-(α-AMINO)-DIOL-DIESTER-CONTAINING POLY (ESTER AMIDE) AND POLY (ESTER URETHANE) COMPOSITIONS AND METHODS OF USE

CROSS REFERENCE TO RELATED APPLICATIONS

This application is a 35 USC §371 National Stage application of International Application No. PCT/US2006/037331 filed Sep. 22, 2006; which claims the benefit under 35 USC §119(e) to U.S. Application Ser. No. 60/839,219 filed Aug. 21, 2006, now abandoned and to U.S. Application Ser. No. 60/719,950 filed Sep. 22, 2005, now abandoned. The disclosure of each of the prior applications is considered part of and is incorporated by reference in the disclosure of this application.

FIELD OF THE INVENTION

The invention relates, in general, to drug delivery systems and, in particular, to polymer delivery compositions that incorporate aliphatic amino acids into a biodegradable polymer backbone.

BACKGROUND INFORMATION

The earliest drug delivery systems, first introduced in the 1970s, were based on polymers formed from lactic and glycolic acids. Today, polymeric materials still provide the most important avenues for research, primarily because they are easy to process and researchers can readily control their chemical and physical properties via molecular synthesis. Basically, two broad categories of polymer systems, both known as "microspheres" because of their size and shape, have been studied: reservoir systems and matrix systems. The former involves the encapsulation of a pharmaceutical product within a polymer shell; whereas the latter describes a system in which a drug is physically entrapped or matrixed within a polymer network.

The release of medications from either category of polymer system traditionally has been diffusion-controlled. Currently, however, modern research is aimed at investigating biodegradable polymer systems. These drug deliverers, for example polyhydroxyalkanoates, degrade into biologically acceptable compounds, often through the process of hydrolysis, and leave their incorporated medications behind. This erosion process occurs either in bulk (wherein the matrix degrades uniformly) or at the polymer's surface (whereby release rates are related to the polymer's surface area). The degradation process itself involves the breakdown of these polymers into lactic and glycolic acids. These acids are eventually reduced by the Kreb's cycle to carbon dioxide and water, which the body can easily expel.

Amino Acid based Bioanalogous Biopolymers (AABB)—a new family of hydrophobic α-amino acid based polymers—recently has been developed. Poly(ester amides), (PEAs) and poly(ester urethanes) (PEURs) with linear structures, which are based on essential α-amino acids, fatty dicarboxylic acids and aliphatic diols have been synthesized via an Active Polycondensation (APC) method. The APC method mainly is conducted in solution under mild temperatures without use of any toxic catalyst. Using this method, a large variety of AABB polymers with a broad range of physical and thermo-mechanical properties and biodegradation profiles have been reported und studied. See review paper and references therein by R. Katsarava (*Macroinol. Symp.* (2003) 199: 419-429).

In particular, amino acid-based poly(ester amide) (PEA) and poly(ester urethane) (PEUR) polymers demonstrate enzyme-mediated surface degradation (G. Tsitlanadze, et al. *J. Biomater. Sci. Polym. Edn.* (2004) 15:1-24) and a low inflammation profile (K. DeFife et al. Transcatheter Cardiovascular Therapeutics—TCT 2004 Conference. Poster presentation. Washington D.C. (2004)). These properties make PEAs and PEURs excellent materials for a variety of different medical and pharmaceutical applications.

Another significant advantage of the APC method is that PEAs and PEURs with programmed physical and mechanical properties as well as biodegradable profiles can be achieved simply by varying three components in the building blocks during their synthesis: naturally occurring amino acids and, therefore, hydrophobic α-amino acids, non-toxic fatty diols and aliphatic dicarboxylic acids. From these components, the following building blocks are built and subjected to the APC method: nucleophilic monomers of bis-α-amino acid)-α,ω-alkylene diesters and bis-electrophiles, which are activated esters of di-acids, for example, bis-(p-nitrophenyl) diesters of fatty di-acids.

Recently, a series of new unsaturated biodegradable PEAs also have been reported, wherein two different types of unsaturation can be introduced into the main backbone: naturally occurring fumaric acid as a di-acid component or 2-butene-1,4-diol-diester as an unsaturated diol partner (K. Guo, et al. Synthesis and Characterization of Novel Biodegradable Unsaturated Poly(ester-amides). *J. Polym. Sci: Part A: Polym. Chem.* (2005) 43:1463-1477). These unsaturated PEAs, particularly polymers based on fumaric acid, showed poor solubility in most organic solvents, high glass transition temperatures in the range of 96° C.-109° C., and sharp melting endotherms in the range of 220° C.-250° C., a thermal profile of that also can be interpreted as indicating simultaneous thermal crosslinking of the polymers.

The physical properties of PEAs and PEURs are heavily dependent on the structure of the polymer backbone, as shown in recent works (Katsarava R, et al. *J. Polym. Sci: Part A: Polymer Chemistry,* 37, 391-407 (1999) and U.S. Pat. No. 6,503,538 B1). For example, replacement of aliphatic diols in the backbone with bicyclic rigid fragments of "sugar-diols"-1,4:3,6-dianhydrohexytols has been shown to significantly increase the glass transition temperature (Tg) of PEAs, providing a glass transition temperature as high as 103° C., while esterase-mediated degradation rates remained in the same order of magnitude as those for other PEAs and PEURs (Z. Gomurashvili, et al. *J. Macromol. Sci. Pure Appl. Chem.* (2000) A37:215-227 and M. Okada et al. *J. Appl. Polym. Sci.* (2001) 81:2721-2734). However, the sugar-diol containing PEAs of this study tend to be unduly rigid.

Thus, there is a need in the art for more and better varieties of biocompatible polymer compositions and methods for delivering therapeutic molecules, such as drugs and other bioactive agents, at a controlled rate of therapeutic or palliative release, while affording enhanced mechanical and physical properties.

SUMMARY OF THE INVENTION

The present invention is based on the discovery of new bis-(α-amino acid)-diol-diester based PEA and PEUR co-polymer compositions containing two bis-α-amino acid)-based building blocks with significant improvement in mechanical properties. Bis-(α-amino acid)-diol-diester is a type of diamine monomer, useful for active polycondensation (APC), and which inherently contains two aliphatic ester linkages. Such ester groups can be enzymatically recognized by various esterases. Condensation of diamine monomers, for example, with activated di-acid esters, results in a PEA macromolecule with ester and amide linkages. Incorporation of a bicyclic-fragment of 1,4:3,6-dianhydrohexitol as the diol residue in at least one of the two bis(α-amino acid)-based building blocks in the invention polymers confers high glass transition temperature (Tg) on the polymer. Incorporation of at least two linear saturated or unsaturated aliphatic diol residues into the two bis-(α amino acid)-based (e.g. bis-(α-amino acid)-diol-diester co-monomers of a PEA), increases the elongation properties of the resulting polymer. Analogously, if at least one of the di-acid residues in the co-polymer is an unsaturated diacid, an increase occurs in the Tg due to polymer self-cross-linking. Similarly, the invention PEUR co-polymers are based on judicious selection of the diol residues used for polycondensation with the bis-(α-amino acid) diester building blocks suitable for a PEUR EU to provide enhanced mechanical properties to the polymers. In addition, the invention PEA and PEUR co-polymer compositions optionally can include a third monomer that is based on a C-protected a directional amino acid monomer to introduce additional flexibility into the polymer and to afford a pendent group suitable for covalent attachment of a bioactive agent, if desired.

Thus the invention provides new PEA and PEUR co-polymers suitable for certain applications requiring a combination of hydrophobicity, relatively high glass transition temperature (Tg), and properties of variable elongation or flexibility. Moreover, since theoretically the bis-α-amino acid)-diol-diester co-monomers in the invention PEA and PEUR co-polymers may each contain a different one of the multiple amino acids disclosed herein in each bis-(α-amino acid) building block, the invention PEA and PEUR co-polymer compositions break down, for example in vivo, to produce from one to multiple different of such α-amino acids.

More particularly, in one embodiment, the invention provides co-polymer compositions containing at least one or a blend of the following:

a PEA having a chemical structure described by general structural formula (I):

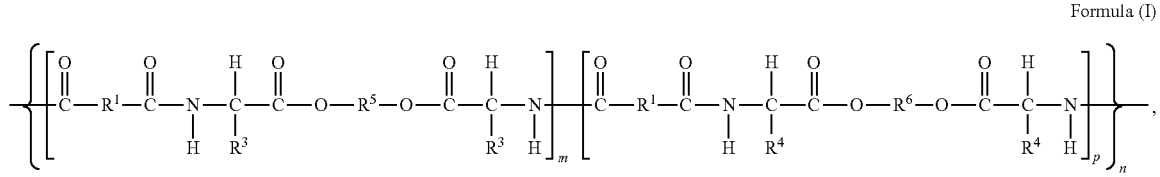

Formula (I)

wherein m is about 0.01 to about 0.99; p is about 0.99 to about 0.01; and wherein n is about 5 to about 100; and wherein $R^1$ is independently selected from the group consisting of ($C_2$-$C_{20}$) alkylene, ($C_2$-$C_{20}$) alkenylene, and combinations thereof; $R^3$s and $R^4$s in a single co-monomer m or p, respectively, are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl and —$(CH_2)_2S(CH_3)$; $R^5$ is selected from bicyclic-fragments of 1,4:3,6-dianhydrohexitols of structural formula (II); and

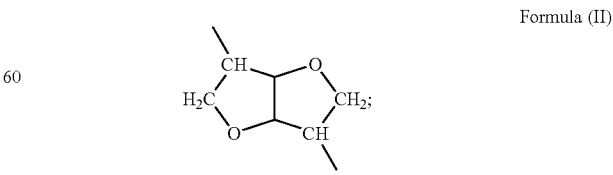

Formula (II)

$R^6$ is selected from the group consisting of ($C_2$-$C_{20}$) alkylene, ($C_2$-$C_{20}$) alkenylene or alkyloxy;

or a PEA having a chemical structure described by general structural formula (III):

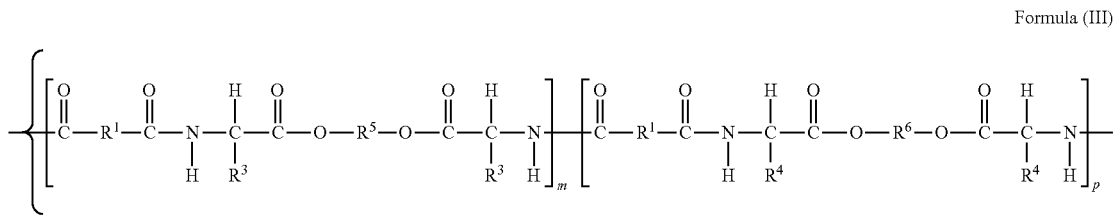

Formula (III)

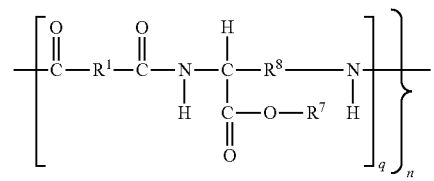

wherein m is about 0.01 to about 0.99; p is about 0.99 to about 0.01; and q is about 0.99 to 0.01; and wherein n is about 5 to about 100; and wherein $R^1$ is independently selected from the group consisting of ($C_2$-$C_{20}$) alkylene, ($C_2$-$C_{20}$) alkenylene, and combinations thereof; $R^3$s and $R^4$s in a single co-monomer m or p, respectively, are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl and —$(CH_2)_2S(CH_3)$; $R^5$ is selected from bicyclic-fragments of 1,4:3,6-dianhydrohexitols of structural formula (II); $R^6$ is selected from the group consisting of ($C_2$-$C_{20}$) alkylene, ($C_2$-$C_{20}$) alkenylene or alkyloxy; $R^7$ is hydrogen, ($C_6$-$C_{10}$) aryl ($C_1$-$C_6$) alkyl or a protecting group; and $R^8$ is independently ($C_1$-$C_{20}$) alkyl or ($C_2$-$C_{20}$) alkenyl;

or a PEUR having a chemical structure described by general structural formula (IV):

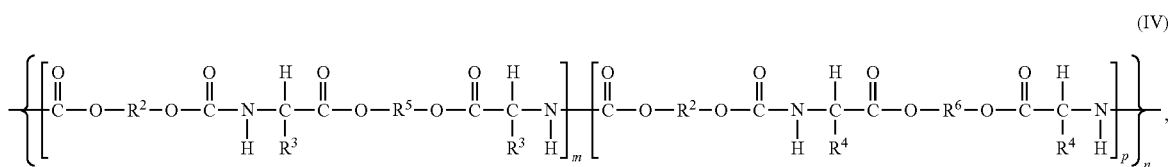

(IV)

wherein m is about 0.01 to about 0.99; p is about 0.99 to about 0.01; and n is about 5 to about 100;

and wherein $R^2$ is selected from the group consisting of ($C_2$-$C_{20}$) alkylene, ($C_2$-$C_{20}$) alkenylene, and bicyclic-fragments of 1,4:3,6-dianhydrohexitols of structural formula (III); the $R^3$s and $R^4$s in a single co-monomer m or p, respectively, are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl, and —$(CH_2)_2S(CH_3)$; $R^5$ is selected from the group consisting of ($C_2$-$C_{20}$) alkylene, and ($C_2$-$C_{20}$) alkenylene or alkyloxy; $R^6$ is selected from bicyclic-fragments of 1,4:3,6-dianhydrohexitols of structural formula (II);

or a PEUR having a chemical structure described by general structural formula (V):

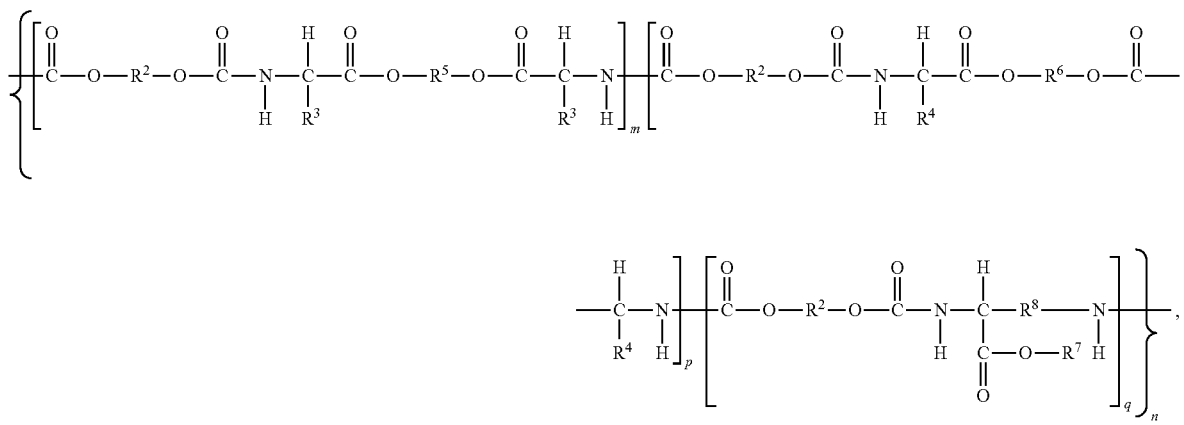

Formula (V)

wherein m is about 0.01 to about 0.99; p is about 0.99 to about 0.01; q is about 0.99 to 0.01; and n is about 5 to about 100;

and wherein $R^2$ is selected from the group consisting of $(C_2-C_{20})$ alkylene, $(C_2-C_{20})$ alkenylene, and bicyclic-fragments of 1,4:3,6-dianhydrohexitols of structural formula (II); the $R^3$s and $R^4$s in a single co-monomer m or p, respectively, are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl, and $-(CH_2)_2S(CH_3)$; $R^5$ is selected from the group consisting of $(C_2-C_{20})$ alkylene, and $(C_2-C_{20})$ alkenylene or alkyloxy; $R^6$ is selected from bicyclic-fragments of 1,4:3,6-dianhydrohexitols of structural formula (II); $R^7$ is hydrogen, $(C_6-C_{10})$ aryl $(C_1-C_6)$ alkyl or a protecting group; and $R^8$ is independently $(C_1-C_{20})$ alkyl or $(C_2-C_{20})$ alkenyl.

In another embodiment, the invention provides methods for fixing an internal body site in a subject by implanting into the internal body site of the subject an internal fixation device made using an invention PEA or PEUR co-polymer composition. The device biodegrades to create substantially biocompatible breakdown products while fixing the internal body site.

In yet another embodiment, the invention provides biodegradable, biocompatible surgical devices fabricated using an invention PEA or PEUR co-polymer composition.

DETAILED DESCRIPTION OF THE INVENTION

The invention describes PEA and PEUR co-polymers based, respectively, on two bis-(α-amino acid)-diol-diester (diester-diamine) containing co-monomers with significant improvement in mechanical properties. While each of the building blocks contributes to the properties of any given PEA or PEUR co-polymer, in the present invention selection of the diol residues in each of the three possible monomer units (including the a directional amino acid-based monomer) is exploited to control the mechanical properties of the co-polymers. Incorporation of a bicyclic-fragment of a 1,4:3,6-dianhydrohexitol as the diol residue in at least one of the two diester-diamine based co-monomers confers relatively high glass transition temperature (Tg) on the co-polymer while introduction of a residue of a saturated or unsaturated alkyl diol in each such co-monomer provides increased elongation properties of the resulting co-polymer (Table 1).

One or a mixture of at least two fatty dicarboxylic acid residues links the two diester-diamines in the invention co-polymers. A third a directional amino acid-based monomer optionally included in an invention co-polymer contains an additional diol residue that can be selected to further control the mechanical properties of the co-polymer as well as providing a pendent group suitable for conjugation of a bioactive agent. These new PEA and PEUR co-polymers exhibit a combination of hydrophobicity, relatively high glass transition temperature (Tg) to confer sufficient stiffness for the co-polymers to be extruded, and also provide sufficient elongation properties to prevent brittleness. Each one of the individual monomer units in the invention PEA and PEUR co-polymer compositions is based on and breaks down during biodegradation to yield one of multiple different α-amino acids, as disclosed herein.

Like other PEA and PEUR polymers, the invention PEA and PEUR co-polymer compositions can be used to deliver in vivo one or more bioactive agents that are dispersed in the co-polymer of the composition. The invention compositions biodegrade in vivo by enzymatic action at the surface of the co-polymer composition so as to release the one or more bioactive agent(s) from the co-polymer in a controlled manner over time.

As used herein, the term "residue of a di-acid" means a portion of a dicarboxylic-acid, as described herein, that excludes the two carboxyl groups of the di-acid. As used herein, the term "residue of a diol" means a portion of a diol, as described herein, which excludes the two hydroxyl groups of the diol. The corresponding di-acid or diol containing the "residue" thereof is used in synthesis of the co-polymer compositions. The residue of the di-acid or diol is reconstituted in vivo (or under similar conditions of pH, aqueous media, and the like) to the corresponding diol or di-acid upon release from the co-polymer composition by biodegradation in a controlled manner that depends upon the properties of the PEA or PEUR co-polymer selected to fabricate the composition, which properties are as described herein, for example in the Examples.

As used herein, the terms "α-amino acid-containing", and "α-amino acid" mean a chemical compound containing an amino group, a carboxyl group and $R_3$ or $R_4$ groups as defined herein. As used herein, the terms "biological α-amino acid-containing" and "biological α amino acid" mean the α-amino acid(s) used in synthesis are naturally occurring L-phenylalanine, leucine, glycine, alanine, valine, isoleucine, lysine, or methionine, or a mixture thereof. Additional biological amino acids used in fabrication of invention co-polymers include lysine and ornithine, but are oriented in the co-polymer backbone a directionally (i.e., in a non-biological orientation) such that the carboxyl group of the amino acid (which may be substituted by an $R^7$ other than H) is pendent rather than being incorporated into a peptide bond. Additional a directional amino acids can be incorporated into the invention compositions by varying the $R^8$ group as described herein.

As used herein the term "bioactive agent" means an agent, for example as described herein, having a therapeutic, healing or palliative effect in mammals, including humans. A bioactive agent as disclosed herein is not incorporated into the co-polymer backbone, but is dispersed within the PEA or PEUR co-polymer. In one embodiment, at least two different bioactive agents are dispersed in the invention co-polymer compositions. As used herein, the term "dispersed" as used to refer to bioactive agents, means the bioactive agents are intermixed, dissolved, or homogenized with, and/or covalently bound to a PEA or PEUR co-polymer in the composition. For example, the bioactive agent can be attached, as described herein, to a functional group in the PEA or PEUR co-polymer of the composition or to the surface of a co-polymer particle or surgical device made using the invention PEA and PEUR co-polymer compositions.

The term, "biodegradable, biocompatible" as used herein to describe the invention PEA and PEUR co-polymer compositions means the co-polymer is capable of being broken down into innocuous products in the normal functioning of the body. Biocompatibility is optimized when the amino acids used in fabrication of the invention co-polymers are biological α-amino acids. In addition, biological enzymes facilitate hydrolysis of ester and cleavage of amide linkages in the invention co-polymer compositions to provide biodegradability. The invention co-polymers are typically chain terminated predominantly with amino groups. Optionally, the amino termini of the co-polymers can be acetylated or otherwise capped by conjugation to any other acid-containing biocompatible molecule, to include without restriction organic acids, bioinactive biologics, other co-polymers, and bioactive agents as described herein. In one embodiment, the entire co-polymer composition, and any particles, or surgical device made thereof, such as an internal fixation device, are substantially biodegradable.

Accordingly, in one embodiment, the invention provides PEA and PEUR co-polymer compositions having a chemical structure described by general structural formula (I): wherein m is about 0.01 to about 0.99; p is about 0.99 to about 0.01; and wherein n is about 5 to about 100; and wherein $R^1$ is independently selected from the group consisting of ($C_2$-$C_{20}$) alkylene, ($C_2$-$C_{20}$) alkenylene, and combinations thereof; $R^3$s and $R^4$s in a single co-monomer m or p, respectively, are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl and —$(CH_2)_2S(CH_3)$; $R^5$ is selected from bicyclic-fragments of 1,4:3,6-dianhydrohexitols of structural formula (II); and

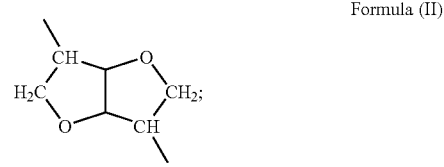

Formula (II)

$R^6$ is selected from the group consisting of ($C_2$-$C_{20}$) alkylene, ($C_2$-$C_{20}$) alkenylene or alkyloxy;

or a PEA having a chemical structure described by general structural formula (III):

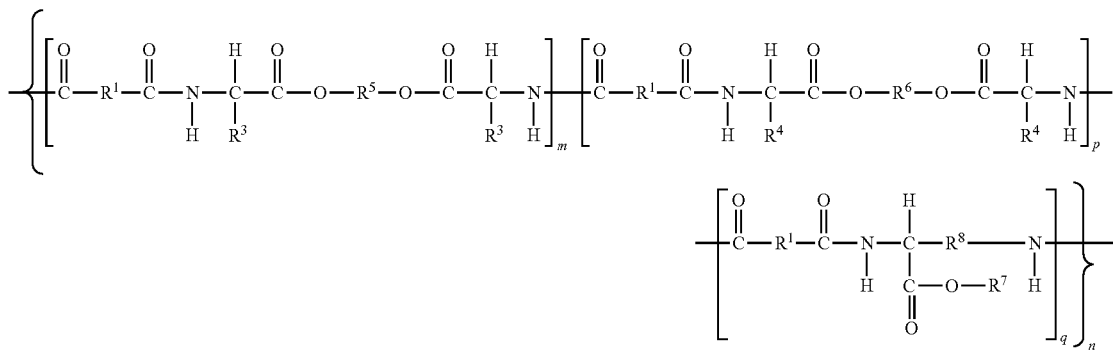

Formula (III)

wherein m is about 0.01 to about 0.99; p is about 0.99 to about 0.01; and q is about 0.99 to 0.01; and wherein n is about 5 to about 100; and wherein $R^1$ is independently selected from the group consisting of ($C_2$-$C_{20}$) alkylene, ($C_2$-$C_{20}$) alkenylene, and combinations thereof; $R^3$s and $R^4$s in a single co-monomer m or p, respectively, are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl and —$(CH_2)_2S(CH_3)$; $R^5$ is selected from bicyclic-fragments of 1,4:3,6-dianhydrohexitols of structural formula (II); $R^6$ is selected from the group consisting of ($C_2$-$C_{20}$) alkylene, ($C_2$-$C_{20}$) alkenylene or alkyloxy; $R^7$ is hydrogen, ($C_6$-$C_{10}$) aryl ($C_1$-$C_6$) alkyl or a protecting group; and $R^8$ is independently ($C_1$-$C_{20}$) alkyl or ($C_2$-$C_{20}$) alkenyl, for example $R^8$ is independently ($C_3$ to $C_6$) alkyl or ($C_3$ to $C_6$) alkenyl;

or a PEUR co-polymer having a chemical structure described by general structural formula (IV):

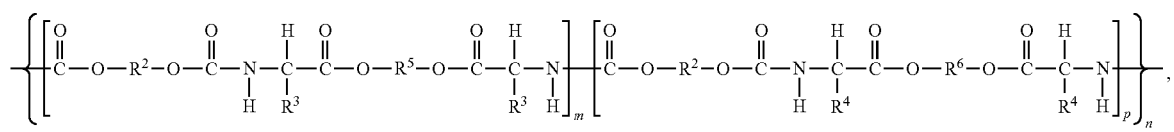
(IV)

wherein m is about 0.01 to about 0.99; p is about 0.99 to about 0.01; and n is about 5 to about 100;

and wherein $R^2$ is selected from the group consisting of $(C_2-C_{20})$ alkylene, $(C_2-C_{20})$ alkenylene, and bicyclic-fragments of 1,4:3,6-dianhydrohexitols of structural formula (III); the $R^3$s and $R^4$s in a single co-monomer m or p, respectively, are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl, and $-(CH_2)_2S(CH_3)$; $R^5$ is selected from the group consisting of $(C_2-C_{20})$ alkylene, and $(C_2-C_{20})$ alkenylene or alkyloxy; $R^6$ is selected from bicyclic-fragments of 1,4:3,6-dianhydrohexitols of structural formula (II);

or a PEUR having a chemical structure described by general structural formula (V):

the biological α amino acid used in synthesis is L-phenylalanine. In alternatives wherein the $R^3$s or $R^4$s are $CH_2-CH(CH_3)_2$, the co-polymer contains the biological α amino acid, leucine. By independently varying the $R^3$s and $R^4$s within variations of the two co-monomers as described herein, other biological α-amino acids can also be used, e.g., glycine (when the $R^3$s or $R^4$s are H), alanine (when the $R^3$s or $R^4$s are $CH_3$), valine (when the $R^3$s or $R^4$s are $CH(CH_3)_2$), isoleucine (when the $R^3$s or $R^4$s are $CH(CH_3)-CH_2-CH_3$), phenylalanine (when the $R^3$s or $R^4$s are $CH_2-C_6H_5$), lysine (when the $R^3$s or $R^4$s $(CH_2)_4-NH_2$); or methionine (when the $R^3$s or $R^4$s are $-(CH_2)_2S(CH_3)$, and mixtures thereof. In yet another embodiment, all of the various α-amino acids contained in the invention PEA and PEUR co-polymers are such biological α-amino acids, as described herein.

The term "aryl" is used with reference to structural formulas herein to denote a phenyl radical or an ortho-fused bicyclic Formula (V)

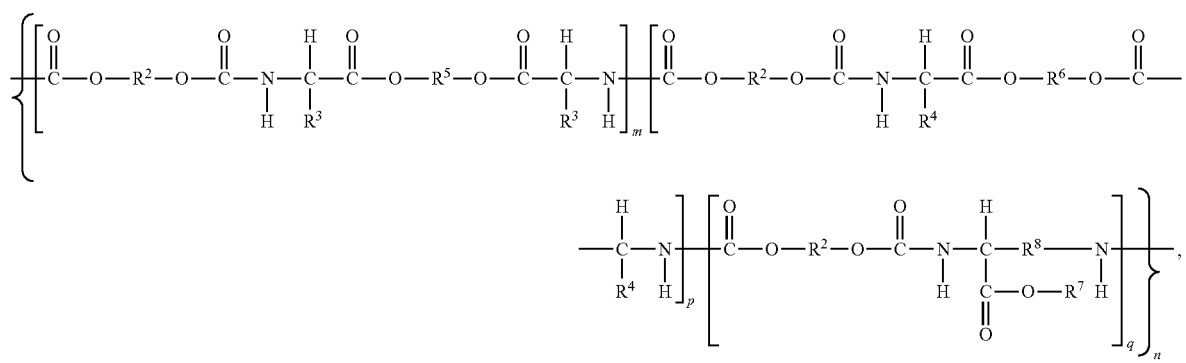

wherein m is about 0.01 to about 0.99; p is about 0.99 to about 0.01; q is about 0.99 to 0.01; and n is about 5 to about 100;

and wherein $R^2$ is selected from the group consisting of $(C_2-C_{20})$ alkylene, $(C_2-C_{20})$ alkenylene, and bicyclic-fragments of 1,4:3,6-dianhydrohexitols of structural formula (II); the $R^3$s and $R^4$s in a single co-monomer m or p, respectively, are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl, and $-(CH_2)_2S(CH_3)$; $R^5$ is selected from the group consisting of $(C_2-C_{20})$ alkylene, and $(C_2-C_{20})$ alkenylene or alkyloxy; $R^6$ is selected from bicyclic-fragments of 1,4:3,6-dianhydrohexitols of structural formula (II); $R^7$ is hydrogen, $(C_6-C_{10})$ aryl $(C_1-C_6)$ alkyl or a protecting group; and $R^8$ is independently $(C_1-C_{20})$ alkyl or $(C_2-C_{20})$ alkenyl.

In one embodiment, $R^8$ is independently $(C_3$ to $C_6)$ alkyl or $(C_3$ to $C_6)$ alkenyl, for example $-(CH_2)_4-$.

In one alternative, at least one of the α-amino acids used in fabrication of the invention co-polymers is a biological α-amino acid. For example, when the $R^3$s or $R^4$s are $CH_2Ph$, carbocyclic radical having about nine to ten ring atoms in which at least one ring is aromatic. In certain embodiments, one or more of the ring atoms can be substituted with one or more of nitro, cyano, halo, trifluoromethyl, or trifluoromethoxy. Examples of aryl include, but are not limited to, phenyl, naphthyl, and nitrophenyl.

The term "alkenylene" is used with reference to structural formulas herein to mean a divalent branched or unbranched hydrocarbon chain containing at least one unsaturated bond in the main chain or in a side chain.

In addition, the co-polymer molecules may optionally have a bioactive agent conjugated thereto via a linker or incorporated into a crosslinker between molecules.

Further, the PEA and PEUR co-polymer compositions suitable for use in the practice of the invention bear functionalities that allow the option of covalent attachment of bioactive agent(s) to the co-polymer.

For example, a co-polymer bearing free carboxyl groups can readily react with an amino moiety, thereby covalently bonding a peptide to the co-polymer via the resulting amide group. As will be described herein, the biodegradable copolymer and a bioactive agent may contain numerous complementary functional groups that can be used to covalently attach the bioactive agent to the biodegradable co-polymer.

Further examples of PEA and PEUR co-polymers related to those contemplated for use in the practice of the invention and methods of synthesis include those set forth in U.S. Pat. Nos. 5,516,881; 5,610,241; 6,476,204; and 6,503,538; and in U.S. application Ser. Nos. 10/096,435; 10/101,408; 10/143,572; 10/194,965 and 10/362,848.

In certain embodiments, particles or a surgical device made from or containing the invention PEA and PEUR co-polymer composition, as described herein, plays an active role in the treatment processes at the site of implant or use by holding the co-polymer and any bioactive agents dispersed therein at the site for a period of time sufficient to allow the subject's endogenous processes to slowly release particles or co-polymer molecules from the implanted composition. Meanwhile, the subject's endogenous processes biodegrade the co-polymer so as to release bioactive agents dispersed in the co-polymer. Fragile bioactive agents dispersed in the invention compositions are protected by the more slowly biodegrading co-polymer to increase half-life and persistence of the bioactive agent(s) locally at the site of use, e.g., implant. A detailed description of methods of making particles using PEA and PEUR co-polymers may be found in co-pending U.S. application Ser. No. 11/344,689, filed Jan. 31, 2006, which is incorporated herein in its entirety.

The invention biodegradable co-polymer compositions preferably have weight average molecular weights ranging from 15,000 to 600,000 Daltons; these copolymers typically have inherent viscosities at 25° C., determined by standard viscosimetric methods, ranging from 0.3 to 3.5, preferably ranging from 0.4 to 2.0

The molecular weights and polydispersities herein are determined by gel permeation chromatography (GPC) using polystyrene standards. More particularly, number and weight average molecular weights ($M_n$ and $M_w$) are determined, for example, using a Model 510 gel permeation chromatographer (Water Associates, Inc., Milford, Mass.) equipped with a high-pressure liquid chromatographic pump, a Waters 486 UV detector and a Waters 2410 differential refractive index detector. Tetrahydrofuran (THF) or N,N-dimethylacetamide (DMAc) is used as the eluent (1.0 mL/min). The polystyrene standards have a narrow molecular weight distribution.

Methods for making co-polymers containing α-amino acids in the structural formula are well known in the art and as described herein. For example, for the embodiment of the co-polymer of formula (I), a α-amino acid can be converted into a bis-(α-amino acid) diester monomer, for example, by condensing the α-amino acid with a diol as described herein. As a result, ester bonds are formed. Then, the bis-(α-amino acid) diester is entered into a polycondensation reaction with a di-acid, such as sebacic acid, to obtain the final co-polymer having both ester and amide bonds. Alternatively, instead of the di-acid, an activated di-acid derivative, e.g., bis-(p-nitrophenyl)diester, can be used as an activated di-acid, for co-polymers of chemical structure (I) or (III).

Additionally, a bis-carbonate, such as bis-(p-nitrophenyl) dicarbonate, can be used as the activated species to obtain co-polymers of structure (IV or V), in which a final co-polymer is obtained having both ester and urethane bonds.

More particularly, synthesis of the unsaturated poly(ester-amide)s (UPEAs) useful as biodegradable co-polymers of the structure (I) or (III) as described above will be described wherein

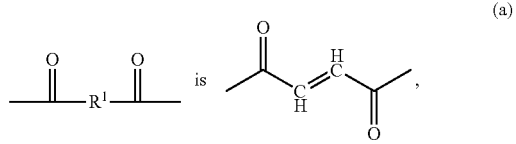

for example, and/or (b) $R^3$ or $R^4$ is —$CH_2$—CH=CH—$CH_2$—. In cases where (a) is present and (b) is not present, $R^3$ or $R^4$ is —$C_4H_8$— or —$C_6H_{12}$—. In cases where (a) is not present and (b) is present, $R^1$ or is —$C_4H_8$— or —$C_8H_{16}$—.

The UPEAs can be prepared by solution polycondensation of either (1) di-p-toluene sulfonic acid salt of bis(α amino acid) diesters, comprising at least 1 double bond in the diol residue, a di-p-toluene sulfonic acid salt of a bis(α amino acid) diesters, comprising a diol of structural formula (III), and di-p-nitrophenyl esters of saturated dicarboxylic acid or (2) two di-p-toluene sulfonic acid salts of bis-(α-amino acid) diesters, comprising no double bonds in the diol residues, and di-nitrophenyl ester of unsaturated dicarboxylic acid or (3) two di-p-toluene sulfonic acid salts of bis-(α-amino acid)-diol-diesters, comprising at least one double bond in one of the diol residues in the co-polymer general structural formula, the other diol residue having structural formula (II), and di-nitrophenyl esters of unsaturated dicarboxylic acids.

Salts of p-toluene sulfonic acid are known for use in synthesizing co-polymers containing amino acid residues. The aryl sulfonic acid salts are used instead of the free base because the aryl sulfonic salts of bis-(α-amino acid)-diol-diesters are easily purified through recrystallization and render the amino groups as unreactive ammonium tosylates throughout workup. In the polycondensation reaction, the nucleophilic amino group is readily revealed through the addition of an organic base, such as triethylamine, so the co-polymer product is obtained in high yield.

For unsaturated co-polymers of structure (I or II), the di-p-nitrophenyl esters of unsaturated dicarboxylic acid can be synthesized from p-nitrophenol and unsaturated dicarboxylic acid chloride, e.g., by dissolving triethylamine and p-nitrophenol in acetone and adding unsaturated dicarboxylic acid chloride dropwise with stirring at −78° C. and pouring into water to precipitate product. Suitable acid chlorides included fumaric, maleic, mesaconic, citraconic, glutaconic, itaconic, ethenyl-butane dioic and 2-propenyl-butandioic acid chlorides. For co-polymers of structure (IV or V), bis-(p-nitrophenyl)dicarbonates of saturated or unsaturated diols are used as the activated monomer. Dicarbonate monomers of general structure (VI) are employed for co-polymers of structure (IV and V)

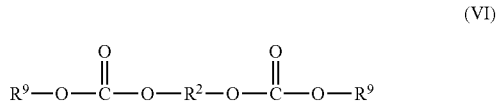

(VI)

wherein each $R^9$ is independently ($C_6$-$C_{10}$) aryl optionally substituted with one or more nitro, cyano, halo, trifluoromethyl, or trifluoromethoxy; and $R^6$ is independently ($C_2$-$C_{20}$) alkylene or ($C_2$-$C_{20}$) alkyloxy, ($C_2$-$C_{20}$) alkenylene or other diol residue having structural formula (II).

The di-aryl sulfonic acid salts of bis-(α-amino acid) diesters of saturated and unsaturated diols can be prepared by admixing α-amino acid, aryl sulfonic acid (e.g., p-toluene sulfonic acid monohydrate) and saturated or unsaturated diol in toluene, heating to reflux temperature, until water evolution is minimal, then cooling. The unsaturated diols include, for example, 2-butene-1,4-diol and 1,18-octadec-9-en-diol.

Saturated bis-(p-nitrophenyl) diesters of dicarboxylic acid and saturated di-p-toluene sulfonic acid salts of bis-α-amino acid) diesters can be prepared as described in U.S. Pat. No. 6,503,538 B1.

Although the invention bis-(α-amino acid)-containing co-polymer compositions are poly(ester amides) (PEAs) and poly(ester urethanes) (PEURs) made by polycondensation of components as described above, in the present invention, the components include a di-p-toluenesulfonic acid salt of bis-(α amino acid)-1,4:3,6-dianhydrosorbitol diester; a di-p-toluenesulfonic acid salt of bis-(α amino acid)-aliphatic α,ω-diol diester and a di-p-nitrophenyl aliphatic (fatty) dicarboxylic acid. By contrast, PEUR co-polymers, of structural formula (V) are made by condensation of at least three components, bis-(α-amino acid) diesters of at least two different types of diols, one of which contains the residue of a bicyclic-fragment of 1,4:3,6-dianhydrohexitol; and one of which is a di-carbonate of one or more fatty acids.

The bis-(p-nitrophenyl) diesters of dicarboxylic acids are used because the p-nitrophenyl ester is a very good leaving group that can promote the condensation reaction to move to the right of the reaction equation so the co-polymer product is obtained in high yield. In addition, the bis-(p-nitrophenyl) diesters are stable throughout workup and can be handled and dried in open atmosphere.

The di-aryl sulfonic acid salts of bis-(α-amino acid) diesters of unsaturated diols can be prepared by admixing α-amino acid, p-aryl sulfonic acid (e.g. p-toluene sulfonic acid monohydrate) and saturated or unsaturated diol in toluene, heating to reflux temperature, until water evolution is minimal, then cooling. The unsaturated diols include, for example, 2-butene-1,4-diol and 1,18-octadec-9-en-diol.

A working example of a diamine monomer having structural formula (III), in U.S. Pat. No. 6,503,538 is provided by substituting p-toluene sulfonic acid salt of bis-(L-phenylalanine)-2-butene-1,4-diester for (III) in Example 1 of U.S. Pat. No. 6,503,538 or by substituting bis-(p-nitrophenyl) fumarate for (V) in Example 1 of U.S. Pat. No. 6,503,538 or by substituting p-toluene sulfonic acid salt of bis-(L-phenylalanine) 2-butene-1,4-diester for III in Example 1 of U.S. Pat. No. 6,503,538 and also substituting bis-(p-nitrophenyl) fumarate for (V) in Example 1 of U.S. Pat. No. 6,503,538.

In unsaturated PEA or PEUR, the following hold: Aminoxyl radical e.g., 4-amino TEMPO can be attached using carbonyldiimidazol, or suitable carbodiimide, as a condensing agent. Optionally, bioactive agents, as described herein, can be attached via a double bond functionality, preferably one that does not occur in a residue of a bioactive agent in the co-polymer backbone. Hydrophilicity, if desired, can be imparted by bonding to poly(ethylene glycol) diacrylate.

The description and methods of synthesis of structurally related PEA and PEUR co-polymers are set forth in U.S. Pat. Nos. 5,516,881; 6,476,204; 6,503,538, the entire content of each of which is incorporated herein by reference.

The PEA and PEUR co-polymers described herein have weight average molecular weights ranging from 15,000 to 600,000 Daltons; these co-polymers typically have inherent viscosities at 25° C., determined by standard viscosimetric methods, ranging from 0.3 to 4.0, preferably ranging from 0.4 to 2.0.

The PEA and PEUR co-polymers described herein can be fabricated in a variety of molecular weights and a variety of relative proportions of the two bis-(α amino acid)-containing units and optional Lysine-based monomer of the co-polymer. The appropriate molecular weight for a particular use is readily determined by one of skill in the art based on the guidelines contained herein and the mechanical properties disclosed. Thus, e.g., a suitable molecular weight will be on the order of about 15,000 to about 600,000 Daltons, for example about 15,000 to about 400,000, or about 15,000 to about 300,000

The invention biodegradable, biocompatible PEA and PEUR copolymers useful in the co-polymer particles, compositions, and biodegradable surgical devices biodegrade by enzymatic action at the surface. Therefore, the co-polymers, for example particles thereof, facilitate in vivo release of a bioactive agent dispersed in the co-polymer at a controlled release rate, which is specific and constant over a prolonged period. Additionally, since PEA and PEUR co-polymers break down in vivo via enzymes without production of adverse side products, the co-polymers in the invention compositions and surgical devices, such as those that produce biological α-amino acids upon break down, are substantially non-inflammatory.

Synthesis of the unsaturated poly(ester-amide)s (UPEAs) useful as biodegradable co-polymers of the structure (I) as described above will now be described. Compounds having the structure (II) can be made in similar fashion to the compound (VII) of U.S. Pat. No. 6,503,538 B1, except that $R^4$ of (III) of 6,503,538 and/or $R^1$ of (V) of U.S. Pat. No. 6,503,538 is $(C_2-C_{20})$ alkenylene as described above. Unsaturated copolymers, co-UPEAs containing different feed ratios of two diamine monomers $R^4$ of (III) of U.S. Pat. No. 6,503,538 will have combinations of above described $(C_2-C_{20})$ alkenylene and residue of 1,4:3,6-dianhydrohexitols. And/or $R^1$ in (V) of U.S. Pat. No. 6,508,538 is $(C_2-C_{20})$ alkenylene, or combinations of alkenylene and fatty acid residues with various feed ratios. Reaction is carried out, for example, by adding dry triethylamine to a mixture of said (III) and (IV) of U.S. Pat. No. 6,503,538 and said (V) of U.S. Pat. No. 6,503,538 in dry N,N-dimethylacetamide, at room temperature, then increasing the temperature to 80° C. and stirring for 16 hours. The reaction solution is then cooled to room temperature, diluted with ethanol, poured into water, co-polymer is separated and washed with water, dried to about 30° C. under reduced pressure and then purified up to negative test on p-nitrophenyl and p-toluene sulfonic acid. A preferred reactant (IV) of U.S. Pat. No. 6,503,538 is p-toluene sulfonic acid salt of lysine benzyl ester, the benzyl ester protecting group is preferably removed from (I) to confer biodegradability, but it should not be removed by hydrogenolysis as in Example 22 of U.S. Pat. No. 6,503,538 because hydrogenolysis would saturate the desired double bonds; rather the benzyl ester group should be converted to an acid group by a method that would preserve unsaturation, e.g., by treatment with fluoroacetic acid or gaseous BF. Alternatively, the lysine reactant (IV) of U.S. Pat. No. 6,503,538 can be protected by a protecting group different from benzyl which can be readily removed in the finished product while preserving unsaturation, e.g., the lysine reactant can be protected with t-butyl (i.e., the reactant can be t-butyl ester of lysine) and the t-butyl can be converted to the "H" form (free carboxylic acid) while preserving unsaturation by treatment of the product (II) with acid.

In unsaturated compounds having structural formula (I) or (III), the following hold: An amino substituted aminoxyl (N-oxide) radical bearing group e.g., 4-amino TEMPO, can be attached using carbonyldiimidazole, or suitable carbodiimide, as a condensing agent. Bioactive agents, and the like, as described herein, optionally can be attached via the double bond functionality. Hydrophilicity can be imparted by bonding to poly(ethylene glycol) diacrylate.

The PEA and PEUR co-polymers and blends thereof contemplated for use in the practice of the invention can be synthesized by a variety of methods well known in the art. For example, tributyltin (IV) catalysts are commonly used to form polyesters such as poly(caprolactone), poly(glycolide), poly(lactide), and the like. However, it is understood that a wide variety of catalysts can be used to form co-polymers suitable for use in the practice of the invention.

Such poly(caprolactones) contemplated for use as above have an exemplary structural formula (VII) as follows:

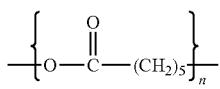

Formula (VII)

tide and ε-caprolactone in the presence of benzyl alcohol using stannous octoate as the catalyst to form a co-polymer of structural formula (X).

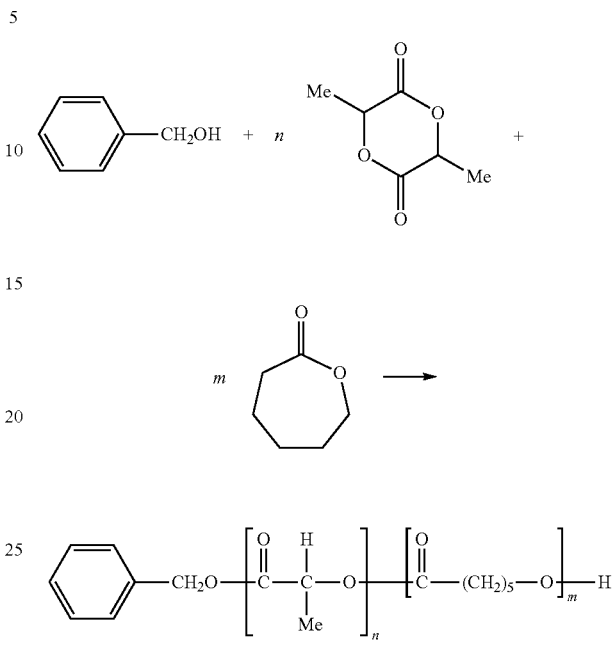

Formula (X)

The hydroxy terminated co-polymer chains can then be capped with maleic anhydride to form co-polymer chains having structural formula (XI):

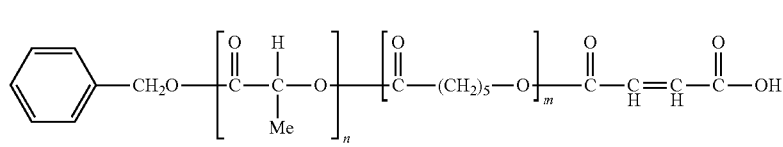

Formula (XI)

Poly(glycolides) contemplated for use have an exemplary structural formula (VIII) as follows:

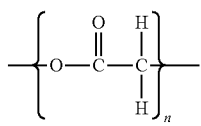

Formula (VIII)

Poly(lactides) contemplated for use have an exemplary structural formula (IX) as follows:

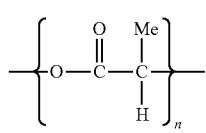

Formula (IX)

An exemplary synthesis of a suitable poly(lactide-co-ε-caprolactone) including an aminoxyl moiety is set forth as follows. The first step involves the copolymerization of lac- At this point, 4-amino-2,2,6,6-tetramethylpiperidine-1-oxy can be reacted with the carboxylic end group to covalently attach the aminoxyl moiety to the copolymer via the amide bond that results from the reaction between the 4-amino group and the carboxylic acid end group. Alternatively, the maleic acid capped copolymer can be grafted with polyacrylic acid to provide additional carboxylic acid moieties for subsequent attachment of further aminoxyl groups.

Due to the versatility of the PEA and PEUR co-polymers used in the invention compositions, the relative amounts of stiffness and elongation properties of the co-polymers as well as the biodegradation rates can be controlled by varying the proportions of the two bis-(α-amino acid)-containing monomers, the a directional amino acid-based monomer and other building blocks of the co-polymer. For example, Table 1 below illustrates the differences in Tg, tensile stress at yield, percent elongation and Young's modulus of PEA co-polymers of structural formula (I) and how relative proportions of the two bis-(a amino acid)-containing monomers in the invention co-polymers affect the various properties. For example, Table 1 below illustrates the properties of copolyesteramides (co-PEAs) composed of adipic acid and various feed ratios of two diamine-diester monomers: bis-(L-leucine)-1,6-hexanediol-diester (Leu(6)) and bis-(L-leucine)-1,4:3,6-dihianhydrosorbitol (Leu(DAS)).

TABLE 1

| Polymer designation | Tg[a] (° C.) | Tensile Stress at Yield (Mpa) | Percent Elongation (%) | Young's Modulus (Mpa) |
|---|---|---|---|---|
| 4-Leu(DAS) | 105.0 | No film formation | | |
| 4-Leu(DAS)75%-Leu(6)25% | 90.7 | 56 | 5 | 2299 |
| 4-Leu(DAS)45%-Leu(6)55% | 69.0 | 39 | 82 | 1431 |
| 4-Leu(DAS)20%-Leu(6)80% | 53.4 | 28 | 339 | 1067 |

[a]Tg was taken from second heating curve with heating rate of 10 C./min by DSC measurement.

Further, as shown in the Examples, addition to any given co-polymer of formulas (I) and (IV) of a third L-lysine-based unit as in structural formulas (II) and (V) (as shown in Table 2 below) will provide an additional measure of percent elongation (%) ("strechability") to the co-polymer, and will vary depending on the nature of the substituent on the C-terminus of L-lysine. In general, the invention PEA and PEUR co-polymers formed as described herein, for example, in the Examples herein, can be expected to have the following mechanical properties.

1. A glass transition temperature in the range from about 22° C. to about 120° C., for example, in the range from about 37° C. to about 80° C.;
2. A film of the co-polymer with an average thickness of about 0.125 mm has a tensile stress at yield of about 25 Mpa to about 90 Mpa, for example, about 30 Mpa to about 60 Mpa;
3. A film of the co-polymer with an average thickness of about 0.125 mm has a percent elongation of about 2% to about 400%, for example about 65% to about 300%; and
4. A film of the co-polymer with an average thickness of about 0.125 mm has a Young's modulus in the range from about 400 Mpa to about 3000 Mpa, for example about 1000 Mpa to about 2500 Mpa.

Thus, by judicious choice of the content and relative proportions of the three building block units, one skilled in the art can obtain an invention bis-(α-amino acid)-containing PEA or PEUR co-polymer that is both biodegradable and biocompatible and which possesses a wide range of mechanical properties.

The designations used to label the PEAs and PEURs in Tables 1 and 2 and in the Examples herein are according to the following formula for each of the primary and secondary bis-(α-amino acid)-containing units of the co-polymer: y-(*)AA$_1$-x$_1$-%-(*)AA$_2$-x$_2$-% wherein y is the number of methylene groups in the dicarboxylic acid residue, (*) indicates the orientation of the following amino acid, x$_1$ indicates the type of bicyclic-fragment of 1, 4:36-dianyhydrohexitol bis-(α-amino acid)-containing unit in one of the bis-(α-amino acid)-containing units and x$_2$ indicates the number of methylene groups in the diol residue of the other bis-(α-amino acid)-containing unit, AA$_1$ and AA$_2$ indicate the α-amino acids in the two bis-(α-amino acid)-containing units. AA$_1$ and AA$_2$ may be identical or different. For example, AA=Phe for phenylalanine ($R^3$ and/or $R^4$=CH$_2$Ph) and Leu for leucine ($R^3$ and/or $R^4$=CH$_2$CH(CH$_3$)$_2$); where y=4 means adipic acid, or y=Fum designates unsaturated fumaric acid. Where x=DAS designates a 1,4:3,6-dianhydrosorbitol. In a similar manner the co-PEA 4-[L-Leu-DAS]$_{0.75}$-[L-Leu-6]$_{0.25}$ (Compound #2, Table 1) means: random co-poly(ester amide), based on adipic acid (y=4) containing 75 mol % of bis-(L-leucine)-1,4:3,6 dianhydrosorbitol-diester and 25% bis-(L-leucine)-1,6-hexanediol-diester.

In certain embodiments, a bioactive agent can be dispersed into the co-polymer by intermixing into the co-polymer solution or by "loading" onto the co-polymer without formation of a chemical bond. Alternatively, a bioactive agent can be linked to any free functional group in the co-polymers, such as an amino, hydroxyl (alcohol), thiol, and the like, to form a direct linkage. Such a linkage can be formed from suitably functionalized starting materials using synthetic procedures that are known in the art.

In certain embodiments, a bioactive agent can be covalently bound to the biodegradable co-polymers via a wide variety of suitable functional groups. For example, when the biodegradable co-polymer is a polyester, the carboxyl group chain end can be used to react with a complimentary moiety on the bioactive agent, such as hydroxy, amino, thio, and the like. A wide variety of suitable reagents and reaction conditions are disclosed, e.g., in *March's Advanced Organic Chemistry, Reactions, Mechanisms, and Structure*, Fifth Edition, (2001); and *Comprehensive Organic Transformations*, Second Edition, Larock (1999).

For example, a co-polymer of the present invention can be linked to the bioactive agent via a carboxyl group (e.g., COOH) of the co-polymer. Specifically, a compound of structures (I and III-VI) can react with an amino functional group of a bioactive agent or a hydroxyl functional group of a bioactive agent to provide a biodegradable, biocompatible co-polymer having the bioactive agent attached via an amide linkage or ester linkage, respectively. In another embodiment, the carboxyl group of the co-polymer of structure (III or VI) wherein $R^7$=H can be transformed into an acyl halide, acyl anhydride/"mixed" anhydride, or active ester.

Alternatively still, the bioactive agent may be attached to the co-polymer via a linker. Indeed, to improve surface hydrophobicity of the biodegradable co-polymer, to improve accessibility of the biodegradable co-polymer towards enzyme activation, and to improve the release profile of the biodegradable co-polymer, a linker may be utilized to indirectly attach the bioactive agent to the biodegradable co-polymer. In certain embodiments, the linker compounds include poly (ethylene glycol) having a molecular weight (Mw) of about 44 to about 10,000, preferably 44 to 2000; amino acids, such as serine; polypeptides with repeat units from 1 to 100; and any other suitable low molecular weight co-polymers. The linker typically separates the bioactive agent from the co-polymer by about 5 angstroms up to about 200 angstroms.

In still further embodiments, the linker is a divalent radical of formula W-A-Q, wherein A is ($C_1$-$C_{24}$) alkyl, ($C_2$-$C_{24}$) alkenyl, ($C_2$-$C_{24}$) alkynyl, ($C_2$-$C_{20}$) alkyloxy, ($C_3$-$C_8$) cycloalkyl, or ($C_6$-$C_{10}$) aryl, and W and Q are each independently —N(R)C(=O)—, —C(=O)N(R)—, —OC(=O)—, —C(=O)O—, —O—, —S—, —S(O), —S(O)$_2$—, —S—S—, —N(R)—, —C(=O)—, wherein each R is independently H or ($C_1$-$C_6$) alkyl.

As used herein, the term "alkyl", as applied to the linkers described herein, refers to a straight or branched chain hydrocarbon group including methyl, ethyl, n-propyl, isopropyl, n-butyl, isobutyl, tert-butyl, n-hexyl, and the like.

As used herein, "alkenyl", as applied to the linkers described herein, refers to straight or branched chain hydrocarbon groups having one or more carbon-carbon double bonds.

As used herein, "alkynyl", as applied to the linkers described herein, refers to straight or branched chain hydrocarbon groups having at least one carbon-carbon triple bond.

As used herein, "aryl", as applied to the linkers described herein, refers to aromatic groups having in the range of 6 up to 14 carbon atoms.

In certain embodiments, the linker may be a polypeptide having from about 2 up to about 25 amino acids. Suitable peptides contemplated for use include poly-L-lysine, poly-L-glutamic acid, poly-L-aspartic acid, poly-L-histidine, poly-L-ornithine, poly-L-threonine, poly-L-tyrosine, poly-L-leucine, poly-L-lysine-L-phenylalanine, poly-L-arginine, poly-L-lysine-L-tyrosine, and the like.

The linker can be attached first to the co-polymer or to the bioactive agent. During synthesis of co-polymers having bioactive agents indirectly attached via a linker, the linker can be either in unprotected form or protected from, using a variety of protecting groups well known to those skilled in the art.

In the case of a protected linker, the unprotected end of the linker can first be attached to the co-polymer or the bioactive agent. The protecting group can then be de-protected using $Pd/H_2$ hydrogenolysis for saturated co-polymers, mild acid or base hydrolysis for unsaturated co-polymers, or any other common de-protection method that is known in the art. The de-protected linker can then be attached to the bioactive agent. An example using poly(ethylene glycol) as the linker is shown in Scheme 1.

Scheme 1: Poly(ethylene glycol) employed as the linker between co-polymer and bioactive agent.

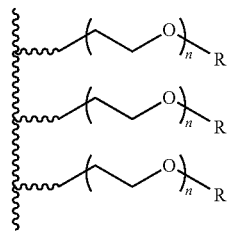

wherein 〰 represents the co-polymer;
R can be a bioactive agent; and
n can range from 1 to 200; preferable from 1 to 50.

An exemplary conjugate synthesis performed on a biodegradable co-polymer according to the invention (wherein the molecule to be attached to the co-polymer is an amino substituted aminoxyl N-oxide radical) is set forth as follows. A biodegradable co-polymer herein can be reacted with an aminoxyl radical containing compound, e.g., 4-amino-2,2,6,6-tetramethylpiperidine-1-oxy, in the presence of N,N'-carbonyl diimidazole or suitable carbodiimide, to replace the hydroxyl moiety in the carboxyl group, either on the pendant carboxylic acids of the PEAs, PEURs or UPEAs, or at the chain end of a polyester as described, with an amide linkage to the aminoxyl (N-oxide) radical containing group. The amino moiety covalently bonds to the carbon of the carbonyl residue such that an amide bond is formed. The N,N'-carbonyldiimidazole or suitable carbodiimide converts the hydroxyl moiety in the carboxyl group at the chain end of the polyester into an intermediate activated moiety which will react with the amino group of the aminoxyl (N oxide) radical compound, e.g., the amine at position 4 of 4-amino-2,2,6,6-tetramethylpiperidine-1-oxy. The aminoxyl reactant is typically used in a mole ratio of reactant to polyester ranging from 1:1 to 100:1. The mole ratio of N,N'-carbonyldiimidazole or carbodiimide to aminoxyl is preferably about 1:1.

A typical reaction is as follows. A polyester is dissolved in a reaction solvent and reaction is readily carried out at the temperature utilized for the dissolving. The reaction solvent may be any in which the polyester will dissolve; this information is normally available from the manufacturer of the polyester. When the polyester is a polyglycolic acid or a poly(glycolide-L-lactide) (having a monomer mole ratio of glycolic acid to L-lactic acid greater than 50:50), highly refined (99.9+% pure) dimethyl sulfoxide at 115° C. to 130° C. or DMSO at room temperature suitably dissolves the polyester. When the polyester is a poly-L-lactic acid, a poly-DL-lactic acid or a poly(glycolide-L-lactide) (having a monomer mole ratio of glycolic acid to L-lactic acid 50:50 or less than 50:50), tetrahydrofuran, dichloromethane (DCM) and chloroform at room temperature to 40~50° C. suitably dissolve the polyester.

The product may be precipitated from the reaction mixture by adding cold non-solvent for the product. For example, aminoxyl-containing polyglycolic acid and aminoxyl-containing poly(glycolide-L-lactide) formed from glycolic acid-rich monomer mixture are readily precipitated from hot dimethylsulfoxide by adding cold methanol or cold acetone/methanol mixture and then recovered, e.g., by filtering. When the product is not readily precipitated by adding cold non-solvent for the product, the product and solvent may be separated by using vacuum techniques. For example, aminoxyl-containing poly-L-lactic acid is advantageously separated from solvent in this way. The recovered product is readily further purified by washing away water and by-products (e.g. urea) with a solvent which does not dissolve the product, e.g., methanol in the case of the modified polyglycolic acid, polylactic acid and poly(glycolide-L-lactide) products herein. Residual solvent from such washing may be removed using vacuum drying.

The invention PEA and PEUR co-polymer compositions can be formulated into particles to provide a variety of properties. The particles can have a variety of sizes and structures suitable to meet differing therapeutic goals and routes of administration using methods described in full in co-pending U.S. application Ser. No. 11/344,689, filed Jan. 31, 2006.

Water soluble covering molecule(s), such as poly(ethylene glycol) (PEG); phosphatidylcholine (PC); glycosaminoglycans including heparin; polysaccharides including chitosan, alginates and polysialic acid; poly(ionizable or polar amino acids) including polyserine, polyglutamic acid, polyaspartic acid, polylysine and polyarginine; as described herein, and targeting molecules, such as antibodies, antigens and ligands, are bioactive agents that can also be conjugated to the co-polymer on the exterior of particles or surgical devices formed from the invention co-polymer compositions after production. Such covering or targeting molecules may be used, respectively, to block active sites on the particles or surgical devices not occupied by a bioactive agent or to target delivery of the particles to a specific body site as is known in the art. The molecular weights of PEG molecules on a single particle can be substantially any molecular weight in the range from about 200 to about 200,000, so that the molecular weights of the various PEG molecules attached to the particle can be varied.

Alternatively, a bioactive agent or covering molecule can be attached to the co-polymer particles or surgical devices made using the invention PEA and PEUR co-polymers via a linker molecule, as described herein. The linker can be attached first to the co-polymer or to the bioactive agent or covering molecule. During synthesis, the linker can be either in unprotected form or protected from, using a variety of protecting groups well known to those skilled in the art. In the case of a protected linker, the unprotected end of the linker can first be attached to the co-polymer particle or surgical device or to the bioactive agent or covering molecule. The protecting group can then be de-protected using Pd/H$_2$ hydrogenation for saturated co-polymer backbones, mild acid or base hydrolysis for unsaturated co-polymers, or any other common de-protection method that is known in the art. The de-protected linker can then be attached to the bioactive agent or covering molecule, or to the co-polymer in the particles or surgical devices.

In an alternative embodiment, a bioactive agent can covalently crosslink molecules of the co-polymer, i.e. the bioactive agent is bound to more than one co-polymer molecule, to form an intermolecular bridge. This covalent crosslinking can be done with or without a linker containing the bioactive agent.

A bioactive agent molecule can also be incorporated into an intramolecular bridge by covalent attachment between two sites on the same co-polymer molecule.

A linear co-polymer/polypeptide conjugate is made by protecting the potential nucleophiles on the polypeptide backbone and leaving only one reactive group to be bound to the co-polymer or co-polymer/linker construct. Deprotection is performed according to methods well known in the art for deprotection of peptides (Boc and Fmoc chemistry for example).

In one embodiment of the present invention, a bioactive agent is a polypeptide presented as a retro-inverso or partial retro-inverso peptide.

In another embodiment, a bioactive agent may be intermixed with (e.g., matrixed with) a photocrosslinkable version of the co-polymer, such as an unsaturated PEA co-polymer and subjected to photo-initiated radical crosslinking. After crosslinking, the co-polymer composition can be dispersed (i.e., ground) to form particles having an average diameter in the range from about 0.1 to about 10 μm.

Polymer—Bioactive Agent Linkage

In one embodiment, PEA and PEUR co-polymer compositions as described herein have one or more bioactive agent directly linked to the co-polymer. The residues of the co-polymer can be linked to the residues of the one or more bioactive agents. For example, one residue of the co-polymer can be directly linked to one residue of a bioactive agent. The co-polymer and the bioactive agent can each have one open valence. Alternatively, more than one bioactive agent, multiple bioactive agents, or a mixture of bioactive agents having different therapeutic or palliative activity, can be directly linked to the co-polymer. However, since the residue of each bioactive agent can be linked to a corresponding residue of the co-polymer, the number of residues of the one or more bioactive agents corresponds to the number of open valences on the residue of the co-polymer.

As used herein, a "residue of a co-polymer" refers to a radical of a PEA or PEUR co-polymer described by formulas (I and III-V) having one or more open valences. Any synthetically feasible atom, atoms, or functional group of the co-polymer (e.g., on the co-polymer backbone or pendant group thereof) is substantially retained when the radical is attached to a residue of a bioactive agent. Additionally, any synthetically feasible functional group (e.g., carboxyl) can be created on the co-polymer (e.g., on the co-polymer backbone, as a pendant group, or as chain termini) to provide the open valence. Based on the linkage that is desired, those skilled in the art can select suitably functionalized starting materials that can be used to derivatize the PEA and PEUR co-polymers used in the present invention using procedures that are known in the art.

For example, the residue of a bioactive agent can be linked to the residue of a compound of structural formula (I, II, IV and V) through an amide (e.g., —N(R)C(=O)— or C(=O)N(R)—), ester (e.g., —OC(=O)— or —C(=O)O—), ether (e.g., —O—), amino (e.g., —N(R)—), ketone (e.g., —C(=O)—), thioether (e.g., —S—), sulfinyl (e.g., —S(O)—), sulfonyl (e.g., —S(O)$_2$—), disulfide (e.g., —S—S—), or a direct (e.g., C—C bond) linkage, wherein each R is independently H or (C$_1$-C$_6$) alkyl. Such a linkage can be formed from suitably functionalized starting materials using synthetic procedures that are known in the art. Based on the linkage that is desired, those skilled in the art can select suitably functional starting material to derivatize any residue of a compound of structural formula (I, II, IV and V) and thereby conjugate a given residue of a bioactive agent using procedures that are known in the art. The residue of the optional bioactive agent can be linked to any synthetically feasible position on the residue of a compound of structural formula (I, II, IV and V). Additionally, the invention also provides compounds having more than one residue of a bioactive agent directly linked to a compound of structural formula (I, II, IV and V).

The number of bioactive agents that can be linked to the co-polymer molecule can typically depend upon the molecular weight of the co-polymer. For example, for a compound of structural formula (I) or (IV), wherein n is about 5 to about 150, preferably about 5 to about 70, up to about 300 bioactive agent molecules (i.e., residues thereof) can be directly linked to the co-polymer (i.e., residue thereof) by reacting the bioactive agent with terminal groups of the co-polymer. On the other hand, for a compound of structural formula (II) or (V) up to an additional 150 bioactive agents can be linked to the co-polymer by reacting the bioactive agent with the pendant group on the Lysine-containing unit. In unsaturated co-polymers, additional bioactive agents can also be reacted with double (or triple) bonds in the co-polymer.

Accordingly, invention co-polymer compositions, either in the form of particles or surgical devices, or not, can be covalently attached directly to the bioactive agent, rather than being dispersed or "loaded" into the co-polymer without chemical attachment, using any of several methods well known in the art and as described hereinabove. The amount of bioactive agent is generally approximately 0.1% to about 60% (w/w) bioactive agent to co-polymer composition, more preferably about 1% to about 25% (w/w) bioactive agent, and even more preferably about 2% to about 20% (w/w) bioactive agent. The percentage of bioactive agent will depend on the desired dose and the condition being treated, as discussed in more detail below.

In addition to serving as a stand-alone delivery system for bioactive agents when directly administered in vivo in the form of implantable particles, the invention PEA and PEUR co-polymer compositions can be used in the fabrication of various types of surgical devices. In this embodiment, the composition from which the surgical device is fabricated is effective for controlled delivery to surrounding tissue of one or more bioactive agents dispersed in the co-polymer in the invention co-polymer composition, for example, covalently attached to the surface thereof.

In one embodiment, the invention PEA or PEUR co-polymer composition has sufficient stiffness to be fabricated in the form of a biodegradable, biocompatible surgical device, including but not limited to internal fixation devices, such as surgical suture, surgical screws, implantable plates, and implantable rods, or as vascular stents and dialysis shunts. Any method known in the art for fabrication of biodegradable co-polymer surgical devices, such as extrusion, injection molding, casting, or solution processing (dry and wet spinning), and the like, can be used for this purpose. Such biodegradable, biocompatible surgical devices slowly biodegrade to create substantially biocompatible breakdown products during biodegradation of the invention device, for example over a period of from about two days to a few years, for example three years, four years or six years, depending on the combination of building blocks selected for the PEA or PEUR co-polymer as well depending on such factors as device shape, thickness, and mode of fabrication.

Accordingly, in another embodiment the invention provides methods for delivering a bioactive agent to a subject comprising implanting at an interior body site an invention surgical device made using an invention PEA or PEUR copolymer, as described herein, so that the device slowly biodegrades, for example completely. A bioactive agent dispersed in the co-polymer used to fabricate the device slowly released to tissue surrounding a site of implantation during biodegradation of the device, for example to promote healing and alleviate pain therein. In embodiments wherein the PEA or PEUR co-polymer used in fabrication of the surgical device is designed to accomplish total biodegradation, no additional surgery is required to remove the implanted surgical device due to its biodegradation properties.

In another embodiment, the invention PEA or PEUR co-polymer composition can be fabricated in the form of a biodegradable, biocompatible pad, sheet or wrap of any desired surface area. For example, the co-polymer can be woven or formed as a thin sheet of randomly oriented fibers by electrospinning to produce nanofibers of the co-polymer. Such pads, sheets and wraps can be used in a number of types of wound dressings for treatment of a variety of conditions, for example by promoting endogenous healing processes at a wound site. The co-polymer composition biodegrades over time, releasing a dispersed bioactive agent to be absorbed into a wound site where it acts intracellularly, either within the cytosol, the nucleus, or both of a target cell, or the bioactive agent can bind to a cell surface receptor molecule to elicit a cellular response without entering the cell. Alternatively, the bioactive agent released from the surgical device, for example when fabricated as a vascular stent, promotes endogenous healing processes at the wound site by contact with the surroundings into which the surgical device is implanted. A detailed description of wound healing implants and surgical device coatings made using PEA and PEUR co-polymers is found in co-pending U.S. patent application Ser. No. 11/128,903, filed May 12, 2005.

Bioactive Agents

Bioactive agents contemplated for dispersion within the co-polymers used in the invention PEA and PEUR co-polymer compositions include anti-proliferants, rapamycin and any of its analogs or derivatives, paclitaxel or any of its taxene analogs or derivatives, everolimus, sirolimus, tacrolimus, or any of its -limus named family of drugs, and statins such as simvastatin, atorvastatin, fluvastatin, pravastatin, lovastatin, rosuvastatin, geldanamycins, such as 17AAG (17-allylamino-17-demethoxygeldanamycin); Epothilone D and other epothilones, 17-dimethylaminoethylamino-17-dimethoxy-geldanamycin and other polyketide inhibitors of heat shock protein 90 (Hsp90), cilostazol, and the like.

Suitable bioactive agents for dispersion in the invention PEA and PEUR co-polymer compositions and particles made therefrom, also can be selected from those that promote endogenous production of a therapeutic natural wound healing agent, such as nitric oxide, which is endogenously produced by endothelial cells. Alternatively the bioactive agents released from the co-polymers during degradation may be directly active in promoting natural wound healing processes by endothelial cells. These bioactive agents can be any agent that donates, transfers, or releases nitric oxide, elevates endogenous levels of nitric oxide, stimulates endogenous synthesis of nitric oxide, or serves as a substrate for nitric oxide synthase or that inhibits proliferation of smooth muscle cells. Such agents include, for example, aminoxyls, furoxans, nitrosothiols, nitrates and anthocyanins; nucleosides such as adenosine and nucleotides such as adenosine diphosphate (ADP) and adenosine triphosphate (ATP); neurotransmitter/neuromodulators such as acetylcholine and 5-hydroxytryptamine (serotonin/5-HT); histamine and catecholamines such as adrenalin and noradrenaline; lipid molecules such as sphingosine-1-phosphate and lysophosphatidic acid; amino acids such as arginine and lysine; peptides such as the bradykinins, substance P and calcium gene-related peptide (CGRP), and proteins such as insulin, vascular endothelial growth factor (VEGF), and thrombin.

A variety of bioactive agents, coating molecules and ligands for bioactive agents can be attached, for example covalently, to the surface of co-polymer particles or surgical devices made using the invention PEA and PEUR co-polymers. Bioactive agents, such as targeting antibodies, polypeptides (e.g., antigens) and drugs can be covalently conjugated to invention co-polymers at the surface of the co-polymer particles or surgical devices. For example, small proteinaceous motifs, such as the B domain of bacterial Protein A and the functionally equivalent region of Protein G are known to bind to, and thereby capture, antibody molecules by the Fc region. Such proteinaceous motifs can be attached as bioactive agents to the invention co-polymers and compositions, especially to the surface of the co-polymer particles described herein. Such molecules will act, for example, as ligands to attach antibodies for use as targeting ligands or to capture antibodies to hold precursor cells or capture cells out of the blood stream. Therefore, the antibody types that can be attached to co-polymer coatings using a Protein A or Protein G functional region are those that contain an Fc region. The capture antibodies will in turn bind to and hold precursor cells, such as progenitor cells, near the co-polymer surface while the precursor cells, which are preferably bathed in a growth medium within the co-polymer, secrete various factors and interact with other cells of the subject. In addition, one or more bioactive agents dispersed in the co-polymer particles, such as the bradykinins, may activate the precursor cells.

In addition, bioactive agents for attaching precursor cells or for capturing progenitor endothelial cells (PECs) from a blood stream in a subject to which the co-polymer compositions are administered are monoclonal antibodies directed against a known precursor cell surface marker. For example, complementary determinants (CDs) that have been reported to decorate the surface of endothelial cells include CD31, CD34, CD102, CD105, CD106, CD109, CDw130, CD141, CD142, CD143, CD144, CDw145, CD146, CD147, and CD166. These cell surface markers can be of varying specificity and the degree of specificity for a particular cell/developmental type/stage is in many cases not fully characterized. In addition, these cell marker molecules against which antibodies have been raised will overlap (in terms of antibody recognition) especially with CDs on cells of the same lineage: monocytes in the case of endothelial cells. Circulating endothelial progenitor cells are some way along the developmental pathway from (bone marrow) monocytes to mature endothelial cells. CDs 106, 142 and 144 have been reported to mark mature endothelial cells with some specificity. CD34 is presently known to be specific for progenitor endothelial cells and therefore is currently preferred for capturing progenitor endothelial cells out of blood in the site into which the co-polymer particles are implanted for local delivery of the active agents. Examples of such antibodies include single-chain antibodies, chimeric antibodies, monoclonal antibodies, polyclonal antibodies, antibody fragments, Fab fragments, IgA, IgG, IgM, IgD, IgE and humanized antibodies, and active fragments thereof.

The following bioactive agents and small molecule drugs will be particularly effective for dispersion within the invention PEA and PEUR co-polymer compositions when selected for their suitable therapeutic or palliative effect with reference to a wound or disease of interest, or symptoms thereof, or in experiments designed for in vitro testing of such effects in cells or tissue culture, or in vivo.

In one embodiment, the suitable bioactive agents are not limited to, but include, various classes of compounds that facilitate or contribute to wound healing when presented in a time-release fashion. Such bioactive agents include wound-healing cells, including certain precursor cells, which can be protected and delivered by the biodegradable co-polymer in the invention compositions. Such wound healing cells include, for example, pericytes and endothelial cells, as well as inflammatory healing cells. To recruit such cells to the site of a co-polymer depot in vivo, the invention PEA and PEUR co-polymer compositions and particles thereof used in the invention and methods of use can include ligands for such cells, such as antibodies and smaller molecule ligands, that specifically bind to "cellular adhesion molecules" (CAMs). Exemplary ligands for wound healing cells include those that specifically bind to Intercellular adhesion molecules (ICAMs), such as ICAM-1 (CD54 antigen); ICAM-2 (CD102 antigen); ICAM-3 (CD50 antigen); ICAM-4 (CD242 antigen); and ICAM-5; Vascular cell adhesion molecules (VCAMs), such as VCAM-1 (CD106 antigen); Neural cell adhesion molecules (NCAMs), such as NCAM-1 (CD56 antigen); or NCAM-2; Platelet endothelial cell adhesion molecules PECAMs, such as PECAM-1 (CD31 antigen); Leukocyte-endothelial cell adhesion molecules (ELAMs), such as LECAM-1; or LECAM-2 (CD62E antigen), and the like.

In another aspect, the suitable bioactive agents include extra cellular matrix proteins, macromolecules that can be dispersed into the co-polymer particles used in the invention PEA and PEUR co-polymer compositions, e.g., attached either covalently or non-covalently. Examples of useful extra-cellular matrix proteins include, for example, glycosaminoglycans, usually linked to proteins (proteoglycans), and fibrous proteins (e.g., collagen; elastin; fibronectins and laminin). Bio-mimics of extra-cellular proteins can also be used. These are usually non-human, but biocompatible, glycoproteins, such as alginates and chitin derivatives. Wound healing peptides that are specific fragments of such extra-cellular matrix proteins and/or their bio-mimics can also be used.

Proteinaceous growth factors are another category of bioactive agents suitable for dispersion in the invention PEA and PEUR co-polymer compositions and methods of use described herein. Such bioactive agents are effective in promoting wound healing and other disease states as is known in the art, for example, Platelet Derived Growth Factor-BB (PDGF-BB), Tumor Necrosis Factor-alpha (TNF-alpha), Epidermal Growth Factor (EGF), Keratinocyte Growth Factor (KGF), Thymosin B4; and, various angiogenic factors such as vascular Endothelial Growth Factors (VEGFs), Fibroblast Growth Factors (FGFs), Tumor Necrosis Factor-beta (TNF-beta), and Insulin-like Growth Factor-1 (IGF-1). Many of these proteinaceous growth factors are available commercially or can be produced recombinantly using techniques well known in the art.

Alternatively, expression systems comprising vectors, particularly adenovirus vectors, incorporating genes encoding a variety of biomolecules can be dispersed in the invention PEA and PEUR co-polymer compositions and particles thereof for timed release delivery. Methods of preparing such expression systems and vectors are well known in the art. For example, proteinaceous growth factors can be dispersed into the invention bioactive compositions for administration of the growth factors either to a desired body site for local delivery, by selection of particles sized to form a co-polymer depot, or systemically, by selection of particles of a size that will enter the circulation. Growth factors, such as VEGFs, PDGFs, FGF, NGF, and evolutionary and functionally related biologics, and angiogenic enzymes, such as thrombin, may also be used as bioactive agents in the invention.

Small molecule drugs are yet another category of bioactive agents suitable for dispersion in the invention PEA and PEUR co-polymer compositions and in methods for delivery described herein. Such drugs include, for example, antimicrobials and anti-inflammatory agents as well as certain healing promoters, such as, for example, vitamin A and synthetic inhibitors of lipid peroxidation.

A variety of antibiotics can be dispersed as bioactive agents in the invention PEA and PEUR co-polymer compositions to indirectly promote natural healing processes by preventing or controlling infection. Suitable antibiotics include many classes, such as aminoglycoside antibiotics, quinolones or beta-lactams, such as cefalosporins, e.g., ciprofloxacin, gentamycin, tobramycin, erythromycin, vancomycin, oxacillin, cloxacillin, methicillin, lincomycin, ampicillin, and colistin. Suitable antibiotics have been described in the literature.

Suitable antimicrobials include, for example, Adriamycin PFS/RDF® (Pharmacia and Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS (Pharmacia and Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology). In one embodiment, the peptide can be a glycopeptide. "Glycopeptide" refers to oligopeptide (e.g. heptapeptide) antibiotics, characterized by a multi-ring peptide core optionally substituted with saccharide groups, such as vancomycin.

Examples of glycopeptides included in this category of antimicrobials may be found in "Glycopeptides Classification, Occurrence, and Discovery," by Raymond C. Rao and Louise W. Crandall, ("Bioactive agents and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327, 5,591,714; 5,840,684; and 5,843,889; in EP 0 802 199; EP 0 801 075; EP 0 667 353; WO 97/28812; WO 97/38702; WO 98/52589; WO 98/52592; and in *J. Amer. Chem. Soc.* (1996) 118: 13107-13108; *J. Amer. Chem. Soc.* (1997) 119:12041-12047; and *J. Amer. Chem. Soc.* (1994) 116:4573-4590. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimyein, Chloroorientiein, Chloropolysporin, Decaplanin, -demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UD-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, including alkylated and acylated derivatives. Additionally, within the scope of this term are glycopeptides that have been further appended with additional saccharide residues, especially aminoglycosides, in a manner similar to vancosamine.

The term "lipidated glycopeptide" refers specifically to those glycopeptide antibiotics that have been synthetically modified to contain a lipid substituent. As used herein, the term "lipid substituent" refers to any substituent contains 5 or more carbon atoms, preferably, 10 to 40 carbon atoms. The lipid substituent may optionally contain from 1 to 6 heteroatoms selected from halo, oxygen, nitrogen, sulfur, and phosphorous. Lipidated glycopeptide antibiotics are well known in the art. See, for example, in U.S. Pat. Nos. 5,840,684, 5,843,889, 5,916,873, 5,919,756, 5,952,310, 5,977,062, 5,977,063, EP 667, 353, WO 98/52589, WO 99/56760, WO 00/04044, WO 00/39156, the disclosures of which are incorporated herein by reference in their entirety.

Anti-inflammatory bioactive agents are also useful for dispersion in invention PEA and PEUR co-polymer compositions and the methods of delivery disclosed herein. Depending on the body site and disease to be treated, such anti-inflammatory bioactive agents include, e.g. analgesics (e.g., NSAIDS and salicylates), steroids, antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, *Physician's Desk Reference*, 2005 Edition. Specifically, the anti-inflammatory agent can include dexamethasone, which is chemically designated as (11∂, 16I)-9-fluoro-11,17,21-trihydroxy-16-methylpregna-1,4-diene-3,20-dione. Alternatively, the anti-inflammatory bioactive agent can be or include sirolimus (rapamycin), which is a triene macrolide antibiotic isolated from *Streptomyces hygroscopicus*.

The polypeptide bioactive agents included in the invention compositions and methods can also include "peptide mimetics." Such peptide analogs, referred to herein as "peptide mimetics" or "peptidomimetics," are commonly used in the pharmaceutical industry with properties analogous to those of the template peptide (Fauchere, J. (1986) *Adv. Bioactive agent Res.*, 15:29; Veber and Freidinger (1985) *TINS*, p. 392; and Evans et al. (1987) *J. Med. Chem.*, 30:1229) and are usually developed with the aid of computerized molecular modeling. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —$CH_2NH$—, —$CH_2S$—, $CH_2$—$CH_2$—, —$CH$=$CH$—(cis and trans), —$COCH_2$—, —$CH(OH)CH_2$—, and —$CH_2SO$—, by methods known in the art and further described in the following references: Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, "Peptide Backbone Modifications" (general review); Morley, J. S., *Trends. Pharm. Sci.*, (1980) pp. 463-468 (general review); Hudson, D. et al., *Int. J. Pept. Prot. Res.*, (1979) 14:177-185 (—$CH_2$ NH—, $CH_2CH_2$—); Spatola, A. F. et al., *Life Sci.*, (1986) 38:1243-1249 (—$CH_2$—S—); Harm, M. M., *J. Chem. Soc. Perkin Trans I* (1982) 307-314 (—$CH$=$CH$—, cis and trans); Almquist, R. G. et al., *J. Med. Chem.*, (1980) 23:2533 (—$COCH_2$—); Jennings-Whie, C. et al., *Tetrahedron Lett.*, (1982) 23:2533 (—$COCH_2$—); Szelke, M. et al., European Appln., EP 45665 (1982) CA: 97:39405 (1982) (—$CH(OH)$ $CH_2$—); Holladay, M. W. et al., *Tetrahedron Lett.*, (1983) 24:4401-4404 (—$C(OH)CH_2$—); and Hruby, V. J., *Life Sci.*, (1982) 31:189-199 (—$CH_2$—S—). Such peptide mimetics may have significant advantages over natural polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Additionally, substitution of one or more amino acids within a peptide (e.g., with a D-Lysine in place of L-Lysine) may be used to generate more stable peptides and peptides resistant to endogenous peptidases. Alternatively, the synthetic polypeptides covalently bound to the biodegradable co-polymer, can also be prepared from D-amino acids, referred to as inverso peptides. When a peptide is assembled in the opposite direction of the native peptide sequence, it is referred to as a retro peptide. In general, polypeptides prepared from D-amino acids are very stable to enzymatic hydrolysis. Many cases have been reported of preserved biological activities for retro-inverso or partial retro-inverso polypeptides (U.S. Pat. No. 6,261,569 B1 and references therein; B. Fromme et al, *Endocrinology* (2003)144:3262-3269.

Any suitable and effective amount of the at least one bioactive agent can be released with time from the invention compositions, including those in a biodegradable internal fixation device, stent, or dialysis shunt, or in a depot formed from particles thereof introduced in vivo. The suitable and effective amount of the bioactive agent will typically depend, e.g., on the specific PEA or PEUR co-polymer and type of particle or co-polymer/bioactive agent linkage, if present. Typically, up to about 100% of the bioactive agent(s) can be released from the invention co-polymer in vivo. Specifically, up to about 90%, up to 75%, up to 50%, or up to 25% thereof can be released from the co-polymer. Factors that typically affect the release rate from the co-polymer are the types of co-polymer/bioactive agent linkage, and the nature and amount of additional substances present in the formulation.

In addition to humans, the invention PEA and PEUR co-polymer compositions, as well as particles and surgical devices fabricated therefrom, are also intended for use in veterinary practice, including a variety of mammalian patients, such as pets (for example, cats, dogs, rabbits, and ferrets), farm animals (for example, swine, horses, mules, dairy and meat cattle) and race horses.

In one embodiment, the invention compositions, devices and methods of administration may release an "effective amount" of one or more bioactive agent(s). That is, an amount of a bioactive agent will be incorporated into the co-polymer thereof that will produce a sufficient therapeutic or palliative response in order to prevent, reduce or eliminate symptoms. The exact amount necessary will vary, depending on the subject to which the composition is being administered; the age and general condition of the subject; the capacity of the subject's immune system, the degree of therapeutic or palliative response desired; the severity of the condition being treated or investigated; the particular bioactive agent selected and the mode of administration of the composition, among other factors. An appropriate effective amount can be readily determined by one of skill in the art. Thus, an "effective amount" will fall in a relatively broad range that can be determined through routine trials. For example, for purposes of the present invention, an effective amount will typically range from about 1 µg to about 100 mg, for example from about 5 µg to about 1 mg, or about 10 µg to about 500 µg of the bioactive agent delivered.

The following examples are meant to illustrate, but not to limit the invention.

Preparation of Invention co-PEAs Based on
bis-(α-amino acid)-diol-diesters

Example 1

This example illustrates preparation of co-poly-4-[Leu(DAS)$_{0.75}$-Leu(6)$_{0.25}$] (Compound #2, of Table 1), which is described by structural formula (I), wherein m=0.75, p=0.25, $R^1=R^2=(CH_2)_4$, $R^3=R^4=$iso-butyl, $R^5=(CH_2)_6$, and $R^6=$formula (III).

Triethylamine (NEt$_3$) (9.67 mL, 0.069 mole) was added to a mixture of di-p-toluenesulfonic acid salt of bis-(L-leucine)-1,4:3,6-dianhydrosorbitol diester (16.9577 g, 0.024 mole); di-p-toluenesulfonic acid salt of bis-(L-leucine)-1,6-hexylene diester (5.4320 g, 0.008 mole); and di-p-nitrophenyl adipate (12.2482 g, 0.032 mole) in dimethylformamide (DMF) (16.61 mL) (total volume of DMF and NEt$_3$ is 26.28 mL, concentration of 1.2 mol/L by di-p-nitrophenyl adipate) at room temperature. Afterwards, the temperature was increased to about 80° C. and stirred for about 24 hours. The viscous reaction solution was cooled to room temperature, diluted with DMF (123.72 mL) (total volume of DMF and NEt$_3$ is 150 mL, concentration of 10% (w/v)). Acetic anhydride (0.567 mL, 0.006 mole) was added and stirred for about 16 hours. The reaction solution was thoroughly washed with water and sodium bicarbonate (1% w/v). For final purification, the co-polymer obtained was dissolved in ethanol (150 mL, 10% w/v). The solution was precipitated in ethyl acetate (1.5 L). Precipitation in the ethyl acetate was repeated until a negative test on p-nitrophenol (a by-product of the polycondensation) was obtained, normally 1-2 times.

The obtained co-polymer was dissolved in ethanol, filtered and dried at about 65° C. under reduced pressure until dry. Yield was 80-90%, $M_w$=211,900 (Gel Permeation Chromatography (GPC) in N,N-dimethylacetamide (DMAc)).

For testing of mechanical properties, as shown in Table 1 above and Table 2 below, dumbbell-shaped films (4×1.6 cm) were cast from chloroform solution, with average thickness of 0.125 mm and subjected to tensile testing on tensile strength machine (Chatillon TDC200) integrated with a PC (Nexygen FM software) at a crosshead speed of 100 mm/min. Glass transition temperatures were determined by Differential Scanning Calorimetry (DSC). Measurements were taken from second heating, heating rate 10° C./min.

Example 2

This example illustrates preparation of poly-4-[L-Leu(DAS)$_{0.45}$-L-Leu(6)$_{0.55}$] (Compound #3, of Table 1), which is described by structural formula (I) wherein m=0.45, q=0.55, $R^1=R^2=(CH_2)_4$, $R^3=R^4=$iso-butyl, $R^5=(CH_2)_6$, $R^6=$formula (III).

Triethylamine (9.85 mL, 0.071 mole) was added to a mixture of di-p-toluenesulfonic acid salt of bis-(L-leucine)-1,4:3,6-dianhydrosorbitol diester (10.3574 g, 0.014 mole); di-p-toluenesulfonic acid salt of bis-(L-leucine)-1,6-hexylene diester (12.1651 g, 0.018 mole); and di-p-nitrophenyl adipate (12.4681 g, 0.032 mole) in DMF (16.91 mL) (total volume of DMF and NEt$_3$ is 26.76 mL, concentration of 1.2 mol/L by di-p-nitrophenyl adipate) at room temperature. Afterwards, the temperature was increased to about 80° C. and stirred for about 24 hours. The viscous reaction solution was cooled to room temperature, diluted with DMF (123.24 mL) (total volume of DMF and NEt$_3$ is 150 mL, concentration of 10% (w/v)). Acetic anhydride (0.567 mL, 0.006 mole) was added and stirred for about 16 hours. The reaction solution was thoroughly washed with water and sodium bicarbonate (1% w/v). For final purification, the co-polymer obtained was dissolved in ethanol (150 mL, 10% w/v). The solution was precipitated in ethyl acetate (1.5 L). Precipitation in ethyl acetate was repeated until a negative test on p-nitrophenol (a by-product of the polycondensation) was obtained, normally 1-2 times.

The obtained co-polymer was dissolved in ethanol, filtered and dried at about 65° C. under reduced pressure until dry. Yield was 80-90%, $M_w$=210,200 (GPC in DMAc).

Example 3

This example illustrates preparation of poly-4-[L-Leu(DAS)$_{0.20}$-L-Leu(6)$_{0.80}$] (Compound #4, of Table 1), which is described by structural formula (I), wherein m 0.20, q=0.80, $R^1=R^2=(CH_2)_4$, $R^3=R^4=$iso-butyl, $R^5=(CH_2)_6$, $R^6=$formula (III).

Triethylamine (9.99 mL, 0.072 mole) was added to a mixture of di-p-toluenesulfonic acid salt of bis-(L-leucine)-1,4:3,6-dianhydrosorbitol diester (4.6732 g, 0.007 mole); di-p-toluenesulfonic acid salt of bis-(L-leucine)-1,6-hexylene diester (17.9636 g, 0.026 mole); and di-p-nitrophenyl adipate (12.6576 g, 0.033 mole) in DMF (17.17 mL) (total volume of DMF and NEt$_3$ is 27.16 mL, concentration of 1.2 mol/L by di-p-nitrophenyl adipate) at room temperature. Afterwards, the temperature was increased to about 80° C. and stirred for about 24 hours. The viscous reaction solution was cooled to room temperature, diluted with DMF (122.84 mL) (total volume of DMF and NEt$_3$ is 150 mL, concentration of 10% (w/v)). Acetic anhydride (0.567 mL, 0.006 mole) was added and stirred for about 16 hours. The reaction solution was thoroughly washed with water and sodium bicarbonate (1% w/v). For final purification, the co-polymer obtained was dissolved in ethanol (150 mL, 10% w/v). The solution was precipitated in ethyl acetate (1.5 L). Precipitation in ethyl acetate was repeated until a negative test on p-nitrophenol (a by-product of the polycondensation) was obtained, normally 1-2 times.

The obtained co-polymer was dissolved in ethanol, filtered and dried at about 65° C. under reduced pressure until dry. Yield was 80-90%, $M_w$=199,200 (GPC in DMAc).

Example 4

This example illustrates preparation of poly-4-[L-Phe(DAS)$_{0.75}$-L-Phe(4)$_{0.25}$] (Compound #2, of Table 2), which is described by structural formula (I) wherein m=0.20, q=0.80, $R^1=R^2=(CH_2)_4$, $R^3=R^4=CH_2(C_6H_5)$, $R^5=(CH_2)_4$, $R^6=$formula (III).

Triethylamine (8.57 mL, 0.061 mole) was added to the mixture of di-p-toluenesulfonic acid salt of bis-(L-phenylalanine)-1,4:3,6-dianhydrosorbitol diester (16.4557 g, 0.021 mole); di-p-toluenesulfonic acid salt of bis-(L-phenylalanine)-1,4-butylene diester (5.0937 g, 0.007 mole); and di-p-nitrophenyl adipate (10.8554 g, 0.028 mole) in dimethylformamide (14.72 mL) (total volume of DMF and NEt$_3$ is 23.30 mL, concentration of 1.2 mol/L by di-p-nitrophenyl adipate) at room temperature. Afterwards, the temperature was increased to about 80° C. and stirred for about 24 hours. The viscous reaction solution was cooled to room temperature, diluted with DMF (126.70 mL) (total volume of DMF and NEt$_3$ is 150 mL, concentration of 10% (w/v)). Acetic anhydride (0.567 mL, 0.006 mole) was added and stirred for about 16 hours. The reaction solution was thoroughly washed with water and sodium bicarbonate (1% w/v). For final purification, the co-polymer obtained was dissolved in THF (150 mL, 10% w/v). The solution was precipitated in ethyl acetate (1.5 L). Precipitation in ethyl acetate was repeated until a negative test on p-nitrophenol (a by-product of the polycondensation) was obtained, normally 1-2 times.

The obtained co-polymer was dissolved in THF, filtered and dried at about 65° C. under reduced pressure until dry. Yield was 80-90%, $M_w$=175,200 (GPC in DMAc).

Preparation of Invention bis-(α-amino acid)-Based PEURs

Example 5

This example illustrates preparation of poly-3-[L-Leu (DAS)$_{0.15}$-L-Leu(6)$_{0.60}$-(L-Lys(Bn)$_{0.25}$] (Compound #3, Table 2), which is described by structural formula (V) wherein p=0.6, m=0.15, q=0.25, $R^8$=$R^9$=(CH$_2$)$_3$, $R^3$=$R^4$=iso-butyl, $R^3$=(CH$_2$)$_6$, $R^9$=formula III, $R^7$=CH$_2$(C$_6$H$_5$). (see scheme 2 below)

was added and stirred for about 16 hours. The reaction solution was thoroughly washed with water and sodium bicarbonate (1% w/v).

For final purification, the co-polymer obtained was dissolved in acetone (150 mL, 10% w/v). The solution was precipitated in ethyl ether (1.5 L). Precipitation in ethyl ether was repeated until a negative test on p-nitrophenol (a by-product of the polycondensation) was obtained, normally 1-2 times. The obtained co-polymer was dissolved in acetone, filtered and dried at about 65° C. under reduced pressure until dry. Yield was 80-90%, $M_w$=78,000 (GPC in DMAc).

Preparation of Unsaturated Co-Peas

Example 6

Preparation of co-poly-[(8)$_{0.75}$-(Fum)$_{0.25}$]-[L-Leu(6)$_{0.50}$-L-Leu(DAS)$_{0.50}$] (Compound #4, Table 1), which is described by formula (I) wherein m=0.50, q=0.50, $R^1$=(CH$_2$)$_8$, $R^2$=(CH$_2$)$_8$-25% and (—CH═CH—)-25%. $R^3$=$R^4$=iso-butyl, $R^5$=(CH$_2$)$_6$, $R^6$=formula (III)).

Triethylamine (2.84 mL, 20.4 mmole) was added to the mixture of di-p-toluenesulfonic acid salt of bis-(L-Leucine)-1,4:3,6-dianhydrosorbitol diester (3.5619 g, 4.968 mmole); di-p-toluenesulfonic acid salt of bis-(L-Leucine)-1,6-hexanediol-diester (3.4229 g, 4.968 mmole); di-p-nitrophenyl-fumarate (0.8901 g, 2.4844 mmole) and di-p-nitrophenyl sebacinate (3.3124 g, 7.453 mmole) in DMF (5.44 mL) (total volume of DMF and NEt$_3$ is 23.30 mL, concentration of 1.2 mol/L by di-p-nitrophenyl adipate) at room temperature. Afterwards, the temperature was increased to about 52° C. and stirred for about 8 hours. The viscous reaction solution Scheme 2.

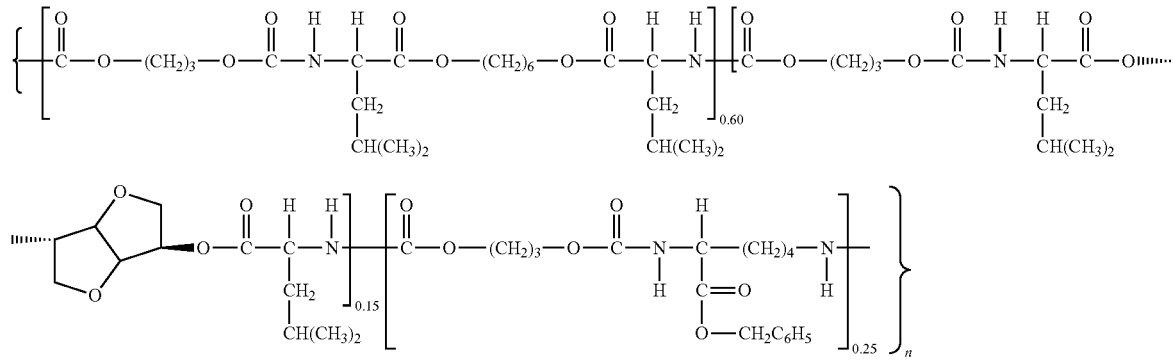

Triethylamine (10.32 mL, 0.0742 mole) was added to a mixture of di-p-toluenesulfonic acid salt of bis-(L-leucine)-1,6-hexylene diester (11.7304 g, 0.0202 mole), di-p-toluenesulfonic acid salt of bis-(L-leucine)-1,4:3,6-dianhydrosorbitol diester (3.5843 g, 0.0050 mole), di-p-toluenesulfonic acid salt of L-lysine benzyl ester (4.8879 g, 0.0084 mole), and propyl biscarbonate (13.6793 g, 0.0336 mole) in DMF (17.73 mL) (total volume of DMF and NEt$_3$ is 28.05 mL, concentration of 1.2 mol/L by the propyl biscarbonate) at room temperature. Afterwards, the temperature was increased to about 80° C. and stirred for about 24 hours. The viscous reaction solution was cooled to room temperature, diluted with DMF (121.95 mL) (total volume of DMF and NEt$_3$ is 150 mL, concentration of 10% (w/v)). Acetic anhydride (0.567 mL)

was cooled to room temperature, diluted with DMF (40 mL) (total volume of DMF and NEt$_3$ is 50 mL, concentration of 10% (w/v)). Acetic anhydride (0.25 mL) was added and stirred for about 3 hours. The viscous co-polymer solution was precipitated in water, washed thoroughly with water and sodium bicarbonate (1% w/v) solution. For final purification, the co-polymer obtained was dissolved in ethanol (150 mL, 10% w/v). The solution was precipitated in ethyl acetate (1.5 L). Yield, 65%, $M_w$=84,000 (GPC in DMAc).

Example 7

The following example illustrates the mechanical and physico-chemical properties of PEAs and PEURs based on different feed ratios of the DAS-containing co-monomer. The relative feed ratios for fabrication of the co-polymers and the properties obtained are as shown in Table 2 below.

TABLE 2

| Compound (#), composition | $M_w{}^{a)} \times 10^{-3}$ | $M_n{}^{a)} \times 10^{-3}$ | $M_w/M_n{}^{a)}$ | $T_g{}^{b)}$ [°C] | % Elongation | Modulus of Elasticity [MPa] |
|---|---|---|---|---|---|---|
| (1), 4-Leu(6)$_{0.75}$Lys(Bn)$_{0.25}$ | 223 | 135 | 1.65 | 45 | 446 | 462 |
| (2), 4-Phe(DAS)$_{0.75}$Phe(4)$_{0.25}$ | 175 | 100 | 1.75 | 90 | 13 | 2600 |
| (3), 3-Leu(DAS)$_{015}$Leu(6)$_{0.60}$ Lys(Bn)$_{0.25}$ | 78 | 52 | 1.50 | 32 | 181 | 425 |
| (4), (8)$_{0.75}$-(Fum)$_{0.25}$- Leu(6)$_{0.50}$-Leu(DAS)$_{0.50}$ | 84 | 43 | 1.95 | 69 | 4 | 1302 |

$^{a)}$GPC Measurements were carried out in DMAc, (PS).
$^{b)}T_g$ was taken from second heating curve with heating rate of 10 C./min by DSC.

All publications, patents, and patent documents are incorporated by reference herein, as though individually incorporated by reference. The invention has been described with reference to various specific and preferred embodiments and techniques. However, it should be understood that many variations and modifications might be made while remaining within the spirit and scope of the invention.

Although the invention has been described with reference to the above examples, it will be understood that modifications and variations are encompassed within the spirit and scope of the invention. Accordingly, the invention is limited only by the following claims.

The invention claimed is:

1. A co-polymer composition comprising at least one co-polymer selected from a member of the group consisting of:

(A) a PEA of structural formula (I):

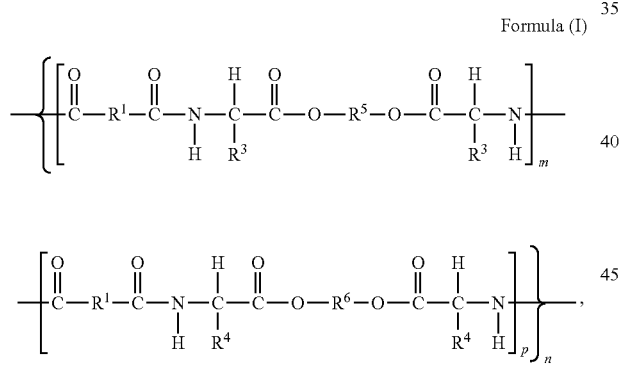

Formula (I)

wherein m is about 0.01 to about 0.99;

p is about 0.99 to about 0.01; and n is about 5 to about 100; and wherein $R^1$ is independently selected from the group consisting of $(C_2-C_{20})$ alkylene, $(C_2-C_{20})$ alkenylene, and combinations thereof; $R^3$s and $R^4$s in a single co-monomer m or p, respectively, are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl and —$(CH_2)_2S(CH_3)$; $R^5$ is selected from bicyclic-fragments of 1,4:3,6-dianhydrohexitols of structural formula (II); and

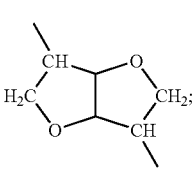

Formula (II)

$R^6$ is selected from the group consisting of $(C_2-C_{20})$ alkylene, $(C_2-C_{20})$ alkenylene or alkyloxy; and (B) a PEA of structural formula (III):

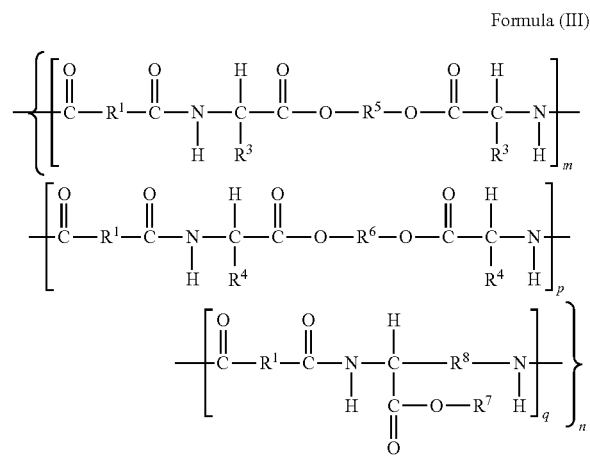

Formula (III)

wherein m is about 0.01 to about 0.99;

p is about 0.99 to about 0.01;

q is about 0.99 to 0.01; and n is about 5 to about 100; and wherein $R^1$ is independently selected from the group consisting of $(C_2-C_{20})$ alkylene, $(C_2-C_{20})$ alkenylene, and combinations thereof; $R^3$s and $R^4$s in a single co-monomer m or p, respectively, are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl and —$(CH_2)_2S(CH_3)$; $R^5$ is selected from bicyclic-fragments of 1,4:3,6-dianhydrohexitols of structural formula (II); $R^6$ is selected from the group consisting of $(C_2-C_{20})$ alkylene, $(C_2-C_{20})$ alkenylene or alkyloxy; $R^7$ is hydrogen, $(C_6-C_{10})$ aryl $(C_1-C_6)$ alkyl or a protecting group; and $R^8$ is independently $(C_1-C_{20})$ alkyl or $(C_2-C_{20})$ alkenyl

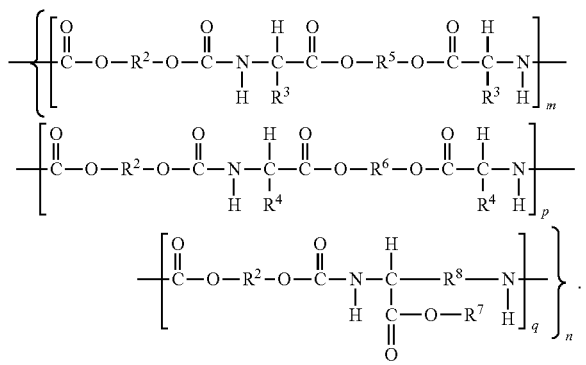

2. The composition of claim 1, wherein at least one of the $R^3$s or $R^4$s in a co-polymer molecule is $CH_2Ph$.

3. The composition of claim 1, wherein the $R^3$s or $R^4$s are selected from hydrogen, $CH_2$—$CH(CH_3)_2$, $CH_3$, $CH(CH_3)_2$, $CH(CH_3)$—$CH_2$—$CH_3$, $CH_2$—$C_6H_5$, $(CH_2)_4$—$NH_2$ or $(CH_2)_2SCH_3$.

4. The composition of claim 1, wherein all of the $R^3$s and $R^4$s are selected from hydrogen, $CH_2$—$CH(CH_3)_2$, $CH_3$, $CH(CH_3)_2$, $CH(CH_3)$—$CH_2$—$CH_3$, $CH_2$—$C_6H_5$, $(CH_2)_4$—$NH_2$ or $(CH_2)_2SCH_3$.

5. The composition of claim 1, wherein at least one of $R^1$ and $R^2$ is selected from —$CH_2$—$CH$=$CH$—$CH_2$—, —$(CH_2)_4$—, —$(CH_2)_6$—, and —$(CH_2)_8$—.

6. The composition of claim 1, wherein at least one $R^5$ and $R^6$ is —$CH_2$—$CH$=$CH$—$C_2$—.

7. The composition of claim 1, wherein the 1,4:3,6-dianhydrohexitol is derived from D-glucitol, D-mannitol, or L-iditol.

8. The composition of claim 1, wherein the 1,4:3,6-dianhydrohexitol is 1,4:3,6-dianhydrosorbitol (DAS).

9. The composition of claim 1, wherein the $R^8$ is ($C_3$-$C_6$) alkenyl.

10. The composition of claim 1, wherein the $R^8$ is —$(CH_2)_4$—.

11. The composition of claim 1, wherein the composition biodegrades over a period of about two days to about six years.

12. The composition of claim 1, wherein the composition biodegrades to form at least two amino acids.

13. The composition of claim 1, wherein the co-polymer has a glass transition temperature (Tg) in the range from about 22 C.° to about 12 C.°.

14. The composition of claim 1, wherein a film of the co-polymer has tensile stress at yield of about 25 Mpa to about 90 Mpa.

15. The composition of claim 1, wherein a film of the co-polymer has a percent elongation of about 2% to about 400% at yield.

16. The composition of claim 1, wherein a film of the co-polymer has a Young's modulus in the range from about 400 Mpa to about 3000 Mpa at yield.

17. The composition of claim 1, wherein the composition further comprises an effective amount of at least one bioactive agent dispersed in the co-polymer.

18. The composition of claim 13, wherein the composition includes from about 5 to about 150 molecules of the bioactive agent per co-polymer molecule chain.

19. The composition of claim 13, wherein the at least one bioactive agent is covalently bonded to the co-polymer.

20. The composition of claim 1, wherein the co-polymer has a molecular weight in the range from about 15,000 Da to about 400,000 Da.

21. The composition of claim 1, wherein the co-polymer has a molecular weight in the range from about 15,000 Da to about 300,000 Da.

22. The composition of claim 1, wherein the co-polymer has a chemical formula described by structural formula I and wherein m and p are randomly distributed within the co-polymer.

23. The composition of claim 1, wherein the co-polymer has a chemical formula described by structural formula III and wherein m, p, and q, are randomly distributed within the co-polymer.

24. The composition of claim 1, wherein the composition is fabricated in the form of biodegradable, biocompatible particles.

* * * * *